United States Patent
Dülk et al.

(10) Patent No.: US 11,791,437 B2
(45) Date of Patent: Oct. 17, 2023

(54) AMPLIFIED SPONTANEOUS EMISSION SEMICONDUCTOR SOURCE

(71) Applicant: EXALOS AG, Schlieren (CH)

(72) Inventors: Marcus Dülk, Schlieren (CH); Nicolai Matuschek, Schlieren (CH)

(73) Assignee: EXALOS AG, Schlieren (CH)

( * ) Notice: Subject to any disclaimer, the term of this patent is extended or adjusted under 35 U.S.C. 154(b) by 680 days.

(21) Appl. No.: 16/731,193

(22) Filed: Dec. 31, 2019

(65) Prior Publication Data
US 2020/0251610 A1    Aug. 6, 2020

(30) Foreign Application Priority Data

Jan. 31, 2019 (GB) .................................. 1901385.3

(51) Int. Cl.
*H01L 33/00* (2010.01)
*A61B 1/06* (2006.01)
(Continued)

(52) U.S. Cl.
CPC ........ *H01L 33/0045* (2013.01); *A61B 1/0684* (2013.01); *A61B 5/0066* (2013.01);
(Continued)

(58) Field of Classification Search
CPC .................. H01L 33/0045; H01S 5/50–509
See application file for complete search history.

(56) References Cited

U.S. PATENT DOCUMENTS

| | | | |
|---|---|---|---|
| 5,200,968 A * | 4/1993 | Kurakake | ............. H01S 5/50 359/344 |
| 5,889,294 A * | 3/1999 | Kashima | ........... H01L 33/0045 257/85 |

(Continued)

FOREIGN PATENT DOCUMENTS

| | | | |
|---|---|---|---|
| CN | 1437289 A | * | 8/2003 |
| CN | 1549354 A | * | 11/2004 |

(Continued)

OTHER PUBLICATIONS

Prokhorov et al., "Broad-Band High-Brightness Light Sources Based on Semiconductor Optical Amplifier and Superluminescent Diode", 2005 ECBO, 68, 1-3. (Year: 2005).*

(Continued)

*Primary Examiner* — Joshua King
(74) *Attorney, Agent, or Firm* — Nemphos Braue LLC; Michael Antone

(57) ABSTRACT

An amplified spontaneous emission, ASE, source device combining a superluminescent light emitting diode, SLED, with a semiconductor optical amplifier, SOA, the SLED and SOA being arranged in series so that the SLED acts as a seed and the SOA acts as a broadband amplifier for the SLED output. Both SLED and SOA have a structure made up of a succession of epitaxial semiconductor layers which form a waveguide comprising a core of active region layers and surrounding cladding layers. The SLED and SOA confinement factors of the SLED and SOA, wherein confinement factor is the percentage of the optical mode power in the active region layers, is designed so that the SLED confinement factor is greater than that of the SOA by at least 20%. This allow higher power outputs, because the SLED power limits imposed by the onset of non-linear effects and catastrophic optical damage can be circumvented.

19 Claims, 19 Drawing Sheets

(51) Int. Cl.
| | |
|---|---|
| *A61B 5/00* | (2006.01) |
| *H01L 33/10* | (2010.01) |
| *H01L 33/32* | (2010.01) |
| *H01L 33/60* | (2010.01) |
| *H01S 5/50* | (2006.01) |
| *H04N 9/31* | (2006.01) |

(52) U.S. Cl.
CPC .............. *H01L 33/10* (2013.01); *H01L 33/32* (2013.01); *H01L 33/60* (2013.01); *H01S 5/50* (2013.01); *H04N 9/315* (2013.01)

(56) References Cited

U.S. PATENT DOCUMENTS

| | | | | |
|---|---|---|---|---|
| 6,184,542 | B1* | 2/2001 | Alphonse | H01L 33/0045 257/94 |
| 6,310,719 | B1* | 10/2001 | Goldstein | H01S 5/5009 359/344 |
| 6,855,571 | B1* | 2/2005 | Sugahara | H01L 21/02378 438/22 |
| 7,215,836 | B2* | 5/2007 | Vakhshoori | H01S 3/302 359/341.1 |
| 9,431,791 | B1 | 8/2016 | Norberg | |
| 10,938,175 | B2* | 3/2021 | Ogoshi | H01S 3/2316 |
| 11,131,795 | B2* | 9/2021 | Dülk | A61B 5/6803 |
| 2002/0131049 | A1* | 9/2002 | Schmitt | G01M 11/3181 356/497 |
| 2004/0017604 | A1 | 1/2004 | Dijaili et al. | |
| 2004/0196540 | A1* | 10/2004 | Lealman | H01S 5/34313 359/344 |
| 2005/0047727 | A1 | 3/2005 | Shin et al. | |
| 2005/0063704 | A1* | 3/2005 | Lee | H04B 10/506 398/66 |
| 2005/0078359 | A1* | 4/2005 | Kim | H01S 5/028 359/344 |
| 2005/0083533 | A1* | 4/2005 | Atia | G01J 3/36 356/454 |
| 2005/0201675 | A1* | 9/2005 | Knopp | G02B 6/4213 385/27 |
| 2006/0072118 | A1 | 4/2006 | Chan et al. | |
| 2007/0096042 | A1 | 5/2007 | Velez et al. | |
| 2007/0153855 | A1* | 7/2007 | Suzuki | H01S 5/34313 257/E33.054 |
| 2007/0223551 | A1* | 9/2007 | Park | H01S 5/0265 372/46.01 |
| 2008/0030845 | A1* | 2/2008 | Dupertuis | H01S 5/026 359/337.2 |
| 2008/0100848 | A1 | 5/2008 | Kobayashi | |
| 2008/0117424 | A1* | 5/2008 | Teramura | A61B 5/0073 356/450 |
| 2008/0137180 | A1* | 6/2008 | Oh | H01L 33/0045 359/344 |
| 2008/0272379 | A1 | 11/2008 | Laino et al. | |
| 2009/0152528 | A1* | 6/2009 | Song | H01L 33/02 438/22 |
| 2009/0154514 | A1 | 6/2009 | Oh et al. | |
| 2010/0193769 | A1* | 8/2010 | Occhi | H01L 33/44 257/E33.048 |
| 2011/0080591 | A1 | 4/2011 | Axsun | |
| 2011/0216795 | A1* | 9/2011 | Hsu | H01L 31/03044 438/31 |
| 2012/0162659 | A1 | 6/2012 | Goldberg et al. | |
| 2012/0207187 | A1* | 8/2012 | Hasegawa | H01S 5/4087 372/50.1 |
| 2012/0257210 | A1 | 10/2012 | Whitney et al. | |
| 2012/0307512 | A1 | 12/2012 | Cogger et al. | |
| 2014/0072002 | A1* | 3/2014 | Connolly | H01S 5/50 372/26 |
| 2014/0153083 | A1 | 6/2014 | Hakimi et al. | |
| 2014/0180012 | A1 | 6/2014 | Yoshino et al. | |
| 2014/0241391 | A1* | 8/2014 | Abe | H01S 5/2202 372/45.01 |
| 2016/0000320 | A1 | 1/2016 | Sharma et al. | |
| 2016/0143520 | A1 | 5/2016 | Masaki et al. | |
| 2016/0322784 | A1* | 11/2016 | Brenot | H01S 5/3434 |
| 2016/0336719 | A1* | 11/2016 | Kiyota | H01S 5/106 |
| 2017/0293134 | A1 | 10/2017 | Otterstrom et al. | |
| 2018/0033910 | A1* | 2/2018 | Watanabe | G09G 3/002 |
| 2018/0156596 | A1 | 6/2018 | Wang et al. | |

FOREIGN PATENT DOCUMENTS

| | | | | |
|---|---|---|---|---|
| CN | 103824920 A | * | 5/2014 | ......... H01L 33/0045 |
| EP | 3648269 A1 | * | 5/2020 | |
| JP | 3558717 B2 | * | 8/2004 | |
| JP | 2008192731 A | * | 8/2008 | |
| JP | 2009283736 A | * | 12/2009 | |
| JP | 2010232371 A | * | 10/2010 | |
| JP | 2015194496 A | * | 11/2015 | |
| KR | 100884353 B1 | * | 2/2009 | |
| WO | 20000005792 | | 2/2000 | |
| WO | 2005038418 | | 4/2005 | |
| WO | 2006039154 | | 4/2006 | |
| WO | WO-2010022526 A2 | * | 3/2010 | |
| WO | 2014084847 | | 6/2014 | |
| WO | WO-2015187046 A1 | * | 12/2015 | ......... H01L 33/0045 |

OTHER PUBLICATIONS

Prokhorov et al., "Broadband Highly Bright Radiation Sources Based on a Superluminescent Diode and a Semiconductor Optical Amplifier", 2005, Quantum Electron. 35, 504-506. (Year: 2005).*

Juodawlkis et al., "Gain-Power Trade-Off in Low-Confinement Semiconductor Optical Amplifiers", 2007, NUSOD, 97-98. (Year: 2007).*

Du et al., High-Power Integrated Superluminescent Light Source, IEEE Journal of Quantum Electronics, vol. 39, No. 1, Jan. 2003.

Shidlovski, Boosting of SLD Power Feedback-Insensitive, Ultra-High-Power MOPA SLD Sources, Application Notes, Superlum @ 2010.

Chamorovskiy, Superlum Benchtop Broadband Light Sources 2016.

Andreeva et al., Single-transverse-mode near-IR superluminescent diodes with cw output power up to 100 mW, Quantum Electronics 44 (10) 903-906 (2014) @ 2014 Kvantovaya Elektronika and Turpion Ltd.

Yamatoya et al, High Power GaInAsP/InP Strained Quantum Well Superluminescent Diode with Tapered Active Region, Jpn. J. Appl. Phys. vol. 38 (1999) pp. 5121-5122, Part 1, No. 9A, Sep. 1999.

* cited by examiner

AMPLIFIED SPONTANEOUS EMISSION SEMICONDUCTOR SOURCE

CROSS-REFERENCE TO RELATED APPLICATIONS

This non-provisional patent application claims the benefit of and priority to U.K. Patent Application No. 1901385.3, filed Jan. 31, 2019, which is incorporated herein by reference in its entirety.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

Field of the Invention

The invention relates to an amplified spontaneous emission (ASE) semiconductor source.

Background

ASE semiconductor sources in the form of superluminescent light emitting diodes (SLEDs) are important for applications where semiconductor laser diodes (LDs) are unsuitable, for example because the coherence of laser light cannot be tolerated or because a broadband emission spectrum is needed. There is increasing demand for higher output powers than are currently available. In particular, for certain applications where a larger area needs to be illuminated, for example for line-field or full-field optical coherence tomography (OCT) systems or for certain machine vision systems or for display systems with larger screens and higher brightness, it would be desirable to realize broadband light sources based on SLEDs with very high output power levels. For example, a SLED-based full-color projector with 150 lm (lumens) of luminous flux could be realized with the following primary colors and output power levels:

Red (R) SLED at 635 nm with 300 mW=~50 lm
Green (G) SLED at 510 nm with 300 mW=~106 lm
Blue (B) SLED at 450 nm with 300 mW=~13 lm For display applications, SLEDs have distinct advantages compared to laser diodes due to their broad optical spectrum and thus short temporal coherence, which dramatically reduces speckle noise and therefore provides sharp and bright images with low intensity noise. For the same reasons, SLEDs are light sources of great interest for machine vision systems. Here, systems that illuminate large areas of an object or systems that scan objects at high throughput and high speed require broadband light sources with high output power levels.

Another field of interest is for certain biomedical imaging applications, for example ophthalmic OCT applications and, particularly, full-field OCT where a larger area would be illuminated. Here, a broadband light source at a center wavelength of 840 nm might be required with:

a large bandwidth (e.g., 20 nm, ideally 40-50 nm);
a high output power (e.g., 200-400 mW); and
single-mode laterally.

The full width half maximum (FWHM) lateral mode size for a semiconductor SLED chip meeting the above specification would be typically 1.5-2.0 µm (roughly 60% of the width of the waveguide ridge) and the vertical mode size would be typically 0.2-0.4 µm (mainly given by the active region of the SLED, consisting of a single quantum well (QW) or multiple quantum wells, and of the cladding layers of the epitaxial structure). However, this SLED specification would give an average optical power density of 20-60 MW/cm2 which would be above the COD (catastrophic optical damage) threshold; and/or above the saturation power, which would result in significant nonlinear effects preventing stable operation.

In other words, it is not possible to make a commercially viable SLED source that meets the above example specifications with current approaches.

SUMMARY OF THE INVENTION

The reason why SLEDs are more limited in their maximum power output compared to LDs is that SLEDs need a higher confinement factor (i.e. smaller mode size). Confinement factor is defined as the percentage of the power of the optical mode that lies within the active region layer, the active region being the region where the carriers for amplified spontaneous emission are located. Typical confinement factor values for LDs are in the range of 0.1% to 1%, which may even correspond to a near circular mode cross-section, whereas for SLEDs they are typically 1-3% and sometimes as high as 10%, corresponding to a very flat mode cross-section.

According to one aspect of the invention there is provided an amplified spontaneous emission, ASE, source device comprising a superluminescent light emitting diode, SLED, and a semiconductor optical amplifier, SOA, arranged in series. Each of the SLED and SOA has a structure made up of a succession of epitaxial semiconductor layers which form an optical mode confining waveguide comprising a core of a higher refractive index active region layer, and a cladding of lower refractive index cladding layers, wherein the SLED and the SOA each have a confinement factor defined as the percentage of the power of the optical mode that lies within the active region layer, wherein the confinement factor of the SLED is greater than that of the SOA by a factor of at least 1.2.

As mentioned above, a relevant parameter for SLED and SOA behavior is confinement factor. As also stated above, confinement factor is defined as the percentage of the power of the optical mode that lies within the active region layer. The confinement factor has components in each of the vertical direction (the direction orthogonal to the semiconductor growth planes), horizontal direction (a direction in the semiconductor growth planes and orthogonal to the light propagation direction along the waveguide) and longitudinal direction (a direction in the semiconductor growth planes and along the light propagation direction along the waveguide). The vertical component of the confinement factor is defined as the percentage of the power of the optical mode in the vertical direction that lies within the active region layer. The lateral component of the confinement factor is defined as the percentage of the power of the optical mode in the horizontal direction that lies within the active region layer. The longitudinal component of the confinement factor is defined as the percentage of the power of the optical mode in the longitudinal direction that lies within the active region layer.

In certain embodiments, the confinement factor of the SLED is greater than that of the SOA by a factor of at least 1.3, 1.4, 1.5 or 2. The confinement factor may also be less than one of 20, 15, 10 or 5, so that desired confinement factor difference ranges may be defined by any combination of 1.2, 1.3, 1.4, 1.5 or 2 as a lower bound and 20, 15, 10 or 5 as an upper bound of the range. In certain embodiments, the vertical component of the confinement factor of the SLED is greater than that of the SOA by a factor of at least 1.2, 1.3, 1.4, 1.5 or 2. The vertical component of the confinement factor may also be less than one of 20, 15, 10 or 5, so that desired vertical component difference ranges may be defined by any combination of 1.2, 1.3, 1.4, 1.5 or 2 as a lower bound and 20, 15, 10 or 5 as an upper bound of the range. In certain embodiments, the lateral component of the confinement factor of the SLED is greater than that of the SOA by a factor of at least 1.2, 1.3, 1.4, 1.5 or 2. The lateral component of the confinement factor may also be less than one of 20, 15, 10 or 5, so that desired lateral component difference ranges may be defined by any combination of 1.2, 1.3, 1.4, 1.5 or 2 as a lower bound and 20, 15, 10 or 5 as an upper bound of the range.

Differences in thickness of the respective active regions of the SLED and SOA can be used to effect differences in the vertical component of the confinement factor. For example, the thickness of the active region layer of the SLED may be greater than that of the SOA by a factor of at least 1.2, 1.3, 1.4, 1.5 or 2. (An upper bound this factor may be 20, 15, 10, 5 or 3 with any of the factors 1.2, 1.3, 1.4, 1.5 or 2 being usable as a lower bound of a range and any of the factors 20, 15, 10, 5 or 3 being usable as an upper bound of said range.)

In certain embodiments, the SLED and the SOA each comprise a ridge. The ridge serves to define the lateral extent of their respective optical modes. In embodiments with these ridge structures, the ridge of the SOA may have a width (or average width if the ridges are not of constant width along their lengths) that is greater than that of the SLED, e.g. by a factor of at least 1.2, 1.3, 1.4, 1.5 or 2. (An upper bound this factor may be 20, 15, 10, 5 or 3 with any of the factors 1.2, 1.3, 1.4, 1.5 or 2 being usable as a lower bound of a range and any of the factors 20, 15, 10, 5 or 3 being usable as an upper bound of said range.)

For embodiments without a ridge, the dimensions of the carrier injection electrodes may define the lateral extent of the optical modes by defining the lateral extent of the presence of carriers in the active region layer. In particular, in such embodiments, the SLED and the SOA may each comprise an injection electrode operable to inject carriers into the active region layer. The electrode width defines the lateral extent of carrier population of the active region which in turn defines the lateral extent of the respective optical modes supported by the respective waveguides of the SLED and SOA.

The SOA may induce spectral narrowing of the SLED output. In this case, the spectral bandwidth of the SLED may be designed to be greater than that of the SOA. The spectral bandwidth may be defined, for example, in terms of the 10 dB power value. In some embodiments, the spectral bandwidth of the SLED may be greater than that of the SOA by at least 20% in wavelength terms. In other embodiments, the bandwidth of the SLED may be the same as, similar to, or smaller than that of the SOA.

There may be benefits to be gained by arranging an optical element in between the SLED and SOA to improve stability of device operation. For example, by arranging an optical isolator between the SLED and SOA, any residual back-travelling light from the SOA is blocked from entering the SLED. Another option is to arrange an optical attenuator between the SLED and SOA, which will attenuate any back-travelling light from the SOA and also require the SLED to be driven with a greater injection current, which may aid stability. A still further option is to arrange a linear polarizer between the SLED and SOA. This could be done in combination with an optical isolator or optical attenuator. This would be useful in embodiments where the SLED and SOA are optimized respectively for emitting and amplifying the horizontal, TE polarization (and not the vertical, TM polarization). The linear polarizer would serve to block any unwanted residual light traveling backwards from the SOA towards the SLED, since the back-travelling light would be TM-polarized. (The reason why the back-travelling light would be TM-polarized is explained further below.)

An advantage of the serial pairing of a SLED and SOA is that these may be fabricated together on a common substrate by a suitable epitaxial growth process for depositing the layers in combination with suitable semiconductor processing. That is, the epitaxial semiconductor layers of the SLED and SOA can be arranged on a common semiconductor substrate. In such an integrated chip embodiment, the SLED and SOA device could each be fabricated with their own p-type metallic contact to inject current, so that the carrier injection for each of the SLED and SOA could still be independently controlled. Another option for serial pairing of the SLED and SOA is for them to be fabricated as separate chips and then arranged on a common submount. Namely, the SLED and SOA may be arranged on separate semiconductor substrates, which are attached to a common submount. This may be an advantage when it is desired to use different materials or materials systems for the SLED and SOA.

Multiple individual SLED-SOA pairs, i.e. ASE source devices as defined above, may be combined into a single module, in which the output from each device is combined within the module, so that the module outputs a single beam that combines the outputs of all the individual ASE source devices.

According to another aspect of the invention there is provided an ASE source module comprising: a first ASE source device as defined above operable to emit a first beam having a first wavelength range; a second ASE source device as defined above operable to emit a second beam having a second wavelength range; and a beam combiner arranged to receive the first and second beams and to combine them into an output beam.

In some embodiments, the first and second wavelength ranges are substantially the same. This may be useful if the aim of combining the beams is to increase power compared to what is achievable with a single ASE source device. This may also be useful if it is desired to have an unpolarized output beam, when each SLED-SOA pair outputs a linearly polarized beam. This can be achieved in one embodiment in which the first and second beams are linearly polarized along respective polarization axes, by arranging the beam combiner to receive the first and second beams with their polarization axes orthogonal to each other so as to combine them into a substantially unpolarized output beam.

In other embodiments, the first and second wavelength ranges are different. Specifically, the first and second wavelength ranges may be chosen to overlap at their ends to produce an output beam having power across a continuous range of wavelengths made up of the combined first and second wavelength ranges. Alternatively, the first and second wavelength ranges may be discontinuous, i.e. have a gap between them in which the combined beam has substantially no power. The wavelength range may be further extended by adding a third or further ASE source devices as defined above, each additional ASE source device having its beam combined with the other output beams using further beam combiners arranged to receive the already combined beams with the additional beam, so that a single combined output beam is produced. For example, with three ASE source devices with respective first, second and third wavelength ranges which are different and overlap at their ends, an output beam may be created having power across a continuous range of wavelengths made up of the combined first, second and third wavelength ranges.

Devices made from one or more ASE sources disclosed herein may find use in a variety of systems.

According to one system aspect of the invention there is provided an optical coherence tomography (OCT) system comprising an ASE source device or module as described herein. In such an OCT system, a beam splitter may be arranged to receive light output from the ASE source device or module and to direct one component into a first, sample arm to a sample position and another component to a second, reference arm, and to recombine light received back from the first and second arms and direct the recombined light to a detector. The OCT system could be for imaging of the eye, for example fundus imaging. The SLED device could act as a RGB (Red-Green-Blue) light source. In a fundus imaging system, an optical arrangement may be provided to direct light output from the ASE source device or module to a sample position and collect light received back from the sample position into a fundus imaging unit.

According to a further system aspect of the invention there is provided an endoscopic imaging system, for example for an endoscope, laparoscope, bronchoscope or catheter system, comprising an ASE source device or module as described herein, for example acting as an RGB light source. The ASE source device or module may be arranged to direct its output into a light guide. Moreover, an insertion tube adapted for insertion into a bodily orifice is provided in which is arranged at least a part of the light guide, wherein the light guide terminates proximal a distal end of the insertion tube.

According to a further system aspect of the invention there is provided a projection system comprising an ASE source module, wherein the ASE source module comprises a first, second and third ASE source devices as disclosed herein operable to emit first to third beams having first to third wavelength ranges; and a beam combiner arranged to receive the first, second and third beams and to combine them into an output beam, wherein the first, second and third wavelength ranges represent three complementary colors of a color palette for additive mixing, e.g. red, green and blue.

While the arrangement of an SOA in series after a SLED is per se known in the patent literature:
WO 2014/084847 A1 (MIT)
US 2014/153083 A1 (MIT)
WO 2005/038418 A3 (Axsun)
US 2011/0080591 A1 (Axsun)
US 2012/0257210 A1 (Axsun)
the optimization of this combination and its realization in an efficient device through engineering of the relative confinement factors of the SLED and SOA is considered to be novel.

BRIEF DESCRIPTION OF THE DRAWINGS

This invention will now be further described, by way of example only, with reference to the accompanying drawings.

DETAILED DESCRIPTION

Figure 1:
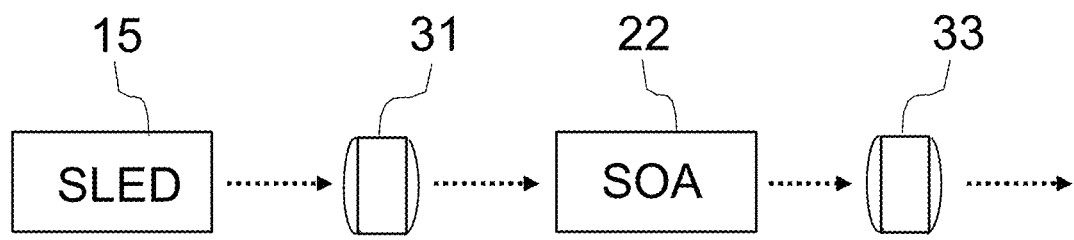
FIG. 1 is a schematic drawing of an ASE source device according to embodiment of the invention comprising a SLED and SOA which are serially connected.

In the following detailed description, for purposes of explanation and not limitation, specific details are set forth in order to provide a better understanding of the present disclosure. It will be apparent to one skilled in the art that the present disclosure may be practiced in other embodiments that depart from these specific details.

As stated in the introduction, the reason why SLEDs are more limited in their maximum power output compared to LDs is that SLEDs need a higher confinement factor (i.e. smaller mode size). This is now discussed in more detail. The confinement factor is defined as the overlap integral between the optical mode and the active region. In principle, the integration has to be performed in all three directions, i.e. vertically, laterally and longitudinally. However, for standard LD and SLED devices the active region is invariant along the ridge (or stripe if there is no ridge), as would be mainly the case if a passive waveguide section were integrated), so the longitudinal overlap integral is unity. Similarly, standard LD and SLED devices are made with an active region that is not realized as a buried heterostructure (BH), so that that the active region extends laterally over the whole chip. Therefore, the lateral overlap integral is also unity. Consequently, the confinement factor is principally defined by the vertical confinement. Here, the overlap integral and hence the confinement factor increases if the optical mode size in the vertical direction decreases (i.e., tighter vertical waveguiding) or if the active region becomes thicker.

In LDs and particularly for high-power LDs the confinement (in vertical direction) of the optical mode is lower compared to SLEDs. Therefore, the vertical mode size is typically larger and, quite often, resembles the mode size in the horizontal direction, thereby resulting in a near circular beam shape output, which is also preferable for aspects like coupling the light output to single-mode waveguides or fibres. Typical confinement numbers for LDs are in the range of 0.1% to 1%, with high-power LDs having rather lower confinement values (i.e. larger mode sizes) in order to increase the damage threshold or nonlinear saturation effects. For comparison, SLEDs have typical confinement numbers in the range of 1-3% but some SLED designs have higher confinement numbers as high as 10% or even more, depending on the thickness of the active region. For example, epitaxial SLED designs with bulk active regions have an active region thickness in the range of 50 nm to 100 nm, or even up to 500 nm, and are considerably thicker compared to designs where only one quantum well (QW) is being used, the QW having a typical thickness of 5-15 nm.

For LDs, the electro-optical efficiency by, for example, the wall-plug efficiency is given by:

$$\eta_{WP} = \frac{P_{out,opt.}}{P_{in,elect.}} = \frac{h\nu}{eV} \cdot \frac{\alpha_m}{\alpha_m + \alpha_i} \cdot \eta_{inj} \cdot \left(1 - \frac{I_{TH}}{I}\right)$$

with $h\nu$ being the photon energy, $\alpha_m$ being the mirror losses, $\alpha_i$ being the internal losses, $\eta_{inj}$ being the injection efficiency (of carriers into the active region), e being the electrical charge unit, I and V being the electrical current and voltage, respectively, and $I_{TH}$ being the lasing threshold current. Standard design optimization strategies for increasing the output power and electro-optical efficiency of a LD are:
  Reduce the forward voltage V across LD device
  Increase the injection efficiency $\eta_{inj}$
  Reduce internal losses $\alpha_i$
  Reduce the lasing threshold $I_{TH}$ Above the lasing threshold, the output power of a LD is only defined by the internal losses, the mirror losses and by the injection efficiency. The optical confinement has no relevance as it only influences the lasing threshold current. As already mentioned, to avoid COD and saturation effects in LDs, the usual strategy is to reduce optical confinement. A reduced optical confinement is also a natural outcome of optimising a LD epitaxial design with respect to the lasing threshold as, typically, the so-called transparency current is minimized. This is achieved by introducing compressive strain into the active region and reducing the number of QWs, often by having only a single QW, thereby also reducing the vertical overlap integral and hence the optical confinement.

In comparison, the output power of a SLED can be expressed as:

$$P_{out} \sim \exp[(g_{mod} - \alpha_i) \cdot L]$$

with L being the length of the active gain segment and $g_{mod}$ being the modal gain, which is defined as:

$$g_{mod} = g_{mat} \cdot \Gamma$$

Here, $g_{mat}$ is the material gain and $\Gamma$ is the confinement factor. This equation demonstrates that, for a SLED, the optical confinement factor has a strong impact on the output power performance and hence on the wall-plug efficiency. Typical design optimization strategies to increase the output power of a SLED are:
  Increase the active-segment length L
  Reduce internal losses $\alpha_i$
  Increase the confinement factor $\Gamma$ Other design parameters might be optimized as well, similar to what is done for LDs, for example reducing the forward voltage to reduce device heating, or increasing the injection efficiency to increase the material gain, which is a function of the current density. Still, it can be understood by comparing the above equations that LD devices are rather optimized to have low optical confinement while SLED devices are rather optimized to have high optical confinement.

On the other hand, a high optical confinement factor reduces the so-called saturation output power Psat, at which the gain and output power start to saturate and nonlinear effects start to become more pronounced:

$$P_{sat} = h\nu \cdot \frac{d \cdot w}{\Gamma} \cdot \frac{1}{g_{diff}} \cdot \frac{1}{\tau_c}$$

Here, d and w refer to the active region's thickness and width, respectively, $g_{diff}$ is the differential gain and $\tau_c$ is the carrier lifetime. This means that for optimising the output power performance of a SLED, a higher confinement factor $\Gamma$ is beneficial as it increases the modal gain, but—at the same time—this limits the maximum achievable output power.

Furthermore, a higher confinement factor for a SLED means a smaller mode size inside the semiconductor structure, which increases the optical power density at the output facet, thereby increasing the risk of COD failure.

To overcome these limitations on output power of SLEDs, we propose an amplified spontaneous emission, ASE, source device in which a semiconductor optical amplifier, SOA, is arranged as a booster after a SLED seed source. The combination of a SLED with SOA allows higher power outputs to be achieved than with a SLED source alone, because the power limits for the SLED imposed by the COD threshold and the onset of non-linear effects caused by saturation can be circumvented.

The design may be optimized by specifying the SOA to have a substantially lower confinement factor than the SLED. This confinement difference between the SLED and SOA can be achieved solely, or if desired mainly, through differences in the vertical confinement, e.g. by having different thicknesses for the respective active regions and/or different refractive index differences between core and clad by careful materials choice for the relevant epitaxial layers. It is also possible to produce a confinement difference by having differing amounts of lateral confinement. Optimization of the proposed ASE source device may thus involve combining a higher-confinement SLED with a lower-confinement SOA. The broadband ASE light output from the SLED is amplified to higher output power levels by an SOA that also supports amplification over a broad spectral range. For example, the SLED may generate ex-facet ASE output power levels of 50, 40, 30, 20, 10, 5, 1 mW and the SOA may generate ex-facet amplified-ASE (AASE) output power levels of 1000, 750, 500, 400, 300, 200, 100, 50, 25 mW with amplification factors of at least 2, 3, 4, 5, 10 or 20 and as much as 100, 75, 50, 40, 30, 20 or 10. Forming an ASE source as proposed by serially connecting a SLED acting as a seeding, lower-power broadband light source followed by a booster SOA for the generation of broadband, high-power light is a combination of optical elements that is capable of generating light output characteristics that are not achievable with a SLED on its own.

It is noted that, when amplifying broadband ASE light in an SOA, some spectral narrowing may occur. Care should therefore be taken with the epitaxial design of the active region of the SOA to limit the spectral narrowing to acceptable levels, so that the SOA supports a broad spectral gain and low spectral narrowing. Typically, narrowing of the spectral gain occurs when the carrier density in the active region (bulk or QW) is reduced by the amplification process. Stronger amplification with high output power levels and, particularly, operation in the strongly-saturated, nonlinear regime of an SOA results in stronger spectral narrowing, which is not desired for applications required a broadband light output. Generation of high output power levels without significant spectral narrowing can be realized with low-confinement epitaxial structures. The reason, as explained above, is that a lower-confinement structure supports a higher nonlinear saturation output power 'Psat' compared to an otherwise equivalent higher-confinement structure.

To serially connect a SLED seeding ASE source to an SOA booster spontaneous emission amplifier there are several options for the optical design of the interconnection. The SLED and SOA can be connected with optical fiber or other waveguide types, such as a planar waveguide. The SLED and SOA can be connected with free-space optics, i.e. lenses and/or mirrors, where the divergent output beam of the SLED is focused into the waveguide of the SOA with an angle equal to or less than the SOA waveguide's acceptance angle to avoid unnecessary losses. The SLED and SOA can also be connected directly. One option to achieve direct connection is by arranging the front facet of the SLED in close proximity to (e.g. with a small gap of, typically, 1-2 μm), or abutting, the rear facet of the SOA such that the output beam from the SLED directly couples into the SOA waveguide. Another option for achieving direct connection is to integrate the SLED and SOA on a single chip. The SLED and SOA could be realized sequentially with different growth steps (and photolithographic processing and etching in between) or in parallel with selective-area growth (SAG). It may also be possible for the SLED and SOA to share the same epitaxial layer structure including the active region layers, where a confinement factor difference can be realized by photolithographic processing after epitaxial growth by having different electrical segments for the carrier injection electrodes for the SLED and SOA, e.g. different widths of the electrodes.

For a light source that is to provide lateral single-mode output, a fiber or integrated waveguide interconnect would also need to support single-mode operation laterally. Furthermore, semiconductor devices are typically polarization-sensitive, which means that the polarization in between the SLED and the SOA will need to be well controlled and stabilized. Some applications may require that the output of the combined light source has a high polarization extinction ratio (PER) and a well-defined (e.g., linear) polarization. Therefore, to meet some more stringent specifications, pairing the two devices with optical single-mode or polarization-maintaining (PM) fibers or integrated waveguide devices might be challenging, since it may become difficult adequately to manage the unwanted effects due to polarization cross-talk or polarization mode mixing or polarization mode dispersion (PMD). A free-space optical connection between a paired SLED and SOA, for example using micro optical lenses on an optical bench technology, avoids the above additional design constraints for fibers and integrated waveguide connections. Semiconductor SLED devices and SOA devices with a broad spectral gain and a spectrally-broad light output will typically support only one polarization, mainly the horizontal or TE polarization. This is partially because the active region is realized with thin QWs (e.g., QW thickness values of 5 to 15 nm) where the spectral gain for TE- and TM-polarized light has very different characteristics. Realizing polarization-insensitive SLED devices and SOA devices would require that the material gain and the confinement for TE- and TM-polarized light be carefully matched, which typically compromises other parameters like broad bandwidth or output power or electro-optical efficiency. Therefore, the natural implementation of the proposed combined SLED-SOA device will be to deliver broadband light output on a single polarization, that single polarization most likely being TE.

A SLED-SOA pair as described herein forms an ASE light source capable of generating and amplifying light over a broad wavelength range. The wavelength range of an individual ASE source as embodied herein may have a value between 3 nm and 100 nm at full width half maximum (FWHM), i.e. 3 dB attenuation level. With future developments in technology it may be possible to broaden the maximum wavelength range. The wavelength range covered by an individual ASE source as disclosed herein may have any value between 3 nm and 160 nm. With current technology and using the arsenide- and phosphide-based materials system wavelength ranges up to 100 nm are achievable in ASE sources with center wavelengths in the near infrared (NIR) and infrared (IR). With current technology and using the nitride-based materials system wavelength ranges up to 30 nm are achievable in blue and green ASE sources. For example, the wavelength range may have a value of 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80 or 90 nm.

FIG. 1 is a schematic drawing of an ASE source device according to embodiments of the invention comprising a SLED 15 and SOA 22 which are serially connected. A lens 31 is shown arranged between the SLED and SOA so as to focus the divergent output beam of the SLED onto an input facet of the SOA. A lens 33 is also shown which collimates (or alternatively focuses to a point outside the module), the divergent output beam from the SOA.

Figure 2:
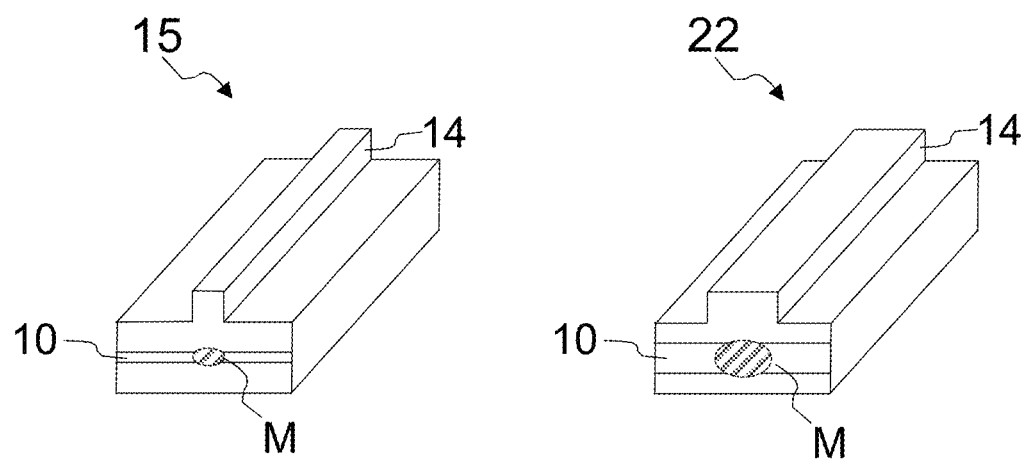
FIG. 2 is a schematic perspective drawing of an example realization of the SLED and SOA.

FIG. 2 is a schematic perspective drawing of a first example realization of the SLED 15 and SOA 22. (The components are shown side-by-side rather than end-to-end for ease of representation only.) The SLED and SOA have respective active regions 10 and ridges 14 as well as optical modes 'M' shown schematically with the cross-hatched ovals. The weaker vertical and lateral confinement of the optical mode in the SOA compared to in the SLED is schematically shown. Both SLED 15 and SOA 22 have a chip structure with front and rear end facets.

The SOA as proposed for the SLED-SOA source disclosed herein is to be implemented as a single-pass device where the light enters at one facet (rear facet) and is emitted from the other facet (front facet). SOAs of this kind are sometimes described as non-resonant, travelling-wave amplifiers. (Here we note that in the literature Fabry-Perot amplifiers based on resonant, multipass cavities are sometimes also referred to as SOAs, but are not SOAs within the meaning of this document.)

For single-pass operation, the SOA front facet should ideally not reflect any light back into the waveguide, so will be coated with an antireflection coating (ARC) to provide a front facet reflectivity, Rf≈0. The front facet may also be tilted relative to the waveguide so that any back-reflection from the end facet does not couple into the waveguide. Similar values for the SOA rear facet reflectivity, Rb, of Rb≈0 are also desired, so an ARC on the rear facet is also desirable. A non-reflecting rear facet of the SOA also serves to minimize coupling losses of the SLED beam into the SOA.

The SLED is designed to operate in a range just above the ASE threshold and just below the lasing threshold with either a single-pass or double-pass design. A single-pass design has Rf≈0 and Rb≈0 as for the SOA, and a double-pass design has a high rear facet reflectivity of Rb≈1 and Rf≈0. The design options are discussed in more detail further below in relation to FIGS. 12A to 12E.

Figure 3:
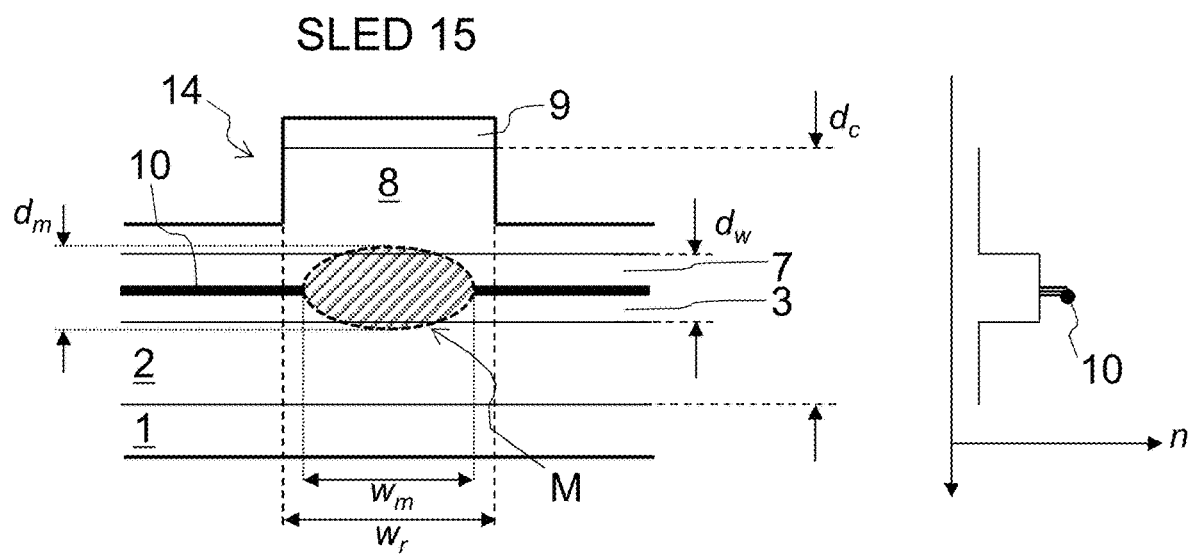
FIG. 3 is a schematic cross-section of a SLED according to one example design.

FIG. 3 is a schematic cross-section of a SLED according to one example design (left-hand part) combined with a schematic graph of the variation of refractive index 'n' with depth (right-hand part). An optical mode 'M' is supported in a waveguide that is defined laterally by the ridge 14 and vertically by the epitaxial design. The epitaxial layers are grown on a substrate 1 by a suitable epitaxy process, such as metallo-organic vapor phase epitaxy (MOVPE) or molecular beam epitaxy (MBE). The layers from the bottom up epitaxially deposited on the substrate 1 are: lower outer cladding layer 2, lower inner cladding layer 3, active regions layer(s) 10, upper inner cladding layer 7, upper outer cladding layer 8 (which extends upwards into a lower part of the ridge 14), and cap layer 9. As shown schematically in the right-hand part of the drawing, the active region layer(s) 10 are of higher refractive index than the inner cladding layers 3, 7, which are, in turn, of higher refractive index than the outer cladding layers 2, 8. In terms of carriers, the outer cladding layers 2, 8 are respectively doped n-type and p-type (or vice versa) to enable carrier injection across the active region layer(s) 10. The active region layer(s) 10 host in operation a reservoir of carriers that are available for spontaneous emission across a suitable band gap of or within the active region, thereby providing the amplification. A functional definition of the active region layer(s) is therefore those layers which, in operation, host carriers that are available for providing amplified spontaneous emission for photons propagating along the waveguide. The (vertical) thickness of the layers 3, 10, 7, collectively referred to as the waveguide layers, is marked as 'dw' and the (vertical) thickness of the fundamental mode of the waveguide is marked as 'dm'. The mode (vertical) thickness is somewhat larger than the waveguide layer thickness owing to the evanescent wave components. Laterally, the (horizontal) width of the ridge is marked as 'wr' and the width of the fundamental mode of the waveguide as 'wm', where in this schematic cross-section wm<wr, although this inequality may be reversed by adjusting the etch depth of the ridge relative to the active region as explained further below. The cladding thickness 'dc' of the device is also marked.

Figure 4:
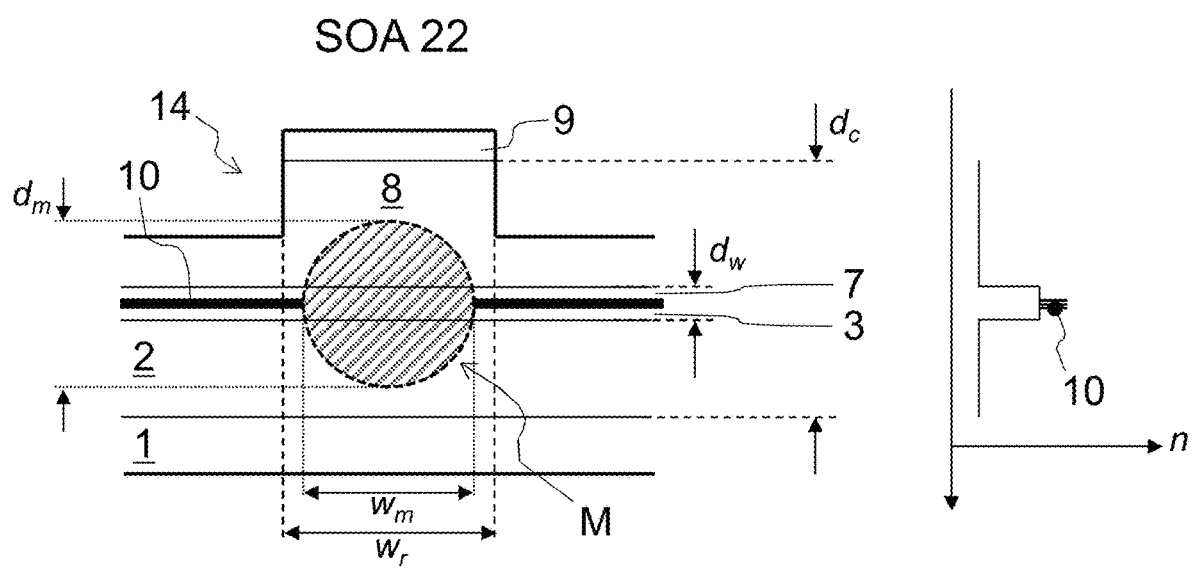
FIG. 4 is a schematic cross-section of an SOA according to one example design.

FIG. 4 is a schematic diagram of an SOA according to one example design (left-hand part) combined with a schematic graph of the variation of refractive index 'n' with depth (right-hand part). Comparing with the SLED of FIG. 3, it can be seen that the vertical confinement of the mode 'M' is weaker. A measure of confinement is a confinement factor defined as the percentage of the power of the optical mode that lies within the active region layer(s). In embodiments of the invention, the confinement factor for the SLED is greater than that of the SOA by a factor of at least 1.2 and in some embodiments more, e.g. 1.3, 1.4, 1.5, 2, 2.5 or 3. The confinement factor is also likely to be less than one of 20, 15, 10 or 5. Comparing FIG. 3 and FIG. 4, these show schematically the situation where the difference in confinement factor is principally achieved through a difference in the vertical confinement, since the respective lateral confinements and the lengthwise confinements along the waveguiding direction (out of the page of the drawing) are substantially the same as each other. This may be expressed by the vertical component of the confinement factor defined as the percentage of the power of the optical mode in the vertical direction that lies within the active region layer(s), wherein the vertical component of the confinement factor of the SLED is greater than that of the SOA, e.g. by a factor of at least 1.2, 1.3, 1.4, 1.5, 2, 2.5 or 3 with a maximum of this ratio being, e.g., less than one of 20, 15, 10 or 5. The degree of vertical confinement can be adjusted by varying the relevant layer thicknesses and/or their refractive index differences.

The waveguide in the SLED and SOA is thus formed by a core and cladding structure in which the active region layers 10 form the core, the inner cladding layers 3 and 7 form the inner cladding and the outer cladding layers 2 and 8 form the outer cladding. Optically, the outer cladding may be insignificant when the evanescent waves of the waveguiding modes decay to zero within the inner cladding. The refractive index choice for the layers 2 and 8 then becomes irrelevant, and these layers solely function to assist the carrier injection. On the other hand, the outer cladding may be significant for the confinement, if the evanescent waves of one or more of the significant waveguiding modes spread into the outer cladding.

One way of providing a different vertical confinement factor for the SLED and SOA is to have different thickness inner cladding layers 3 and 7. The SOA may have thinner cladding layers 3, 7 and hence lower vertical confinement, than the SLED. Another way of providing a different vertical confinement factor for the SLED and SOA is to have different refractive indices for the inner cladding layers 3 and 7. The SOA may have lower refractive index inner cladding layers 3, 7 and hence lower vertical confinement, than the SLED.

Independently of providing the desired confinement difference between SLED and SOA through different levels of vertical confinement, achieved through varying the epitaxial wafer structures between the SLED and SOA, the lateral confinement can also be used to generate a confinement difference. Lateral confinement can be defined by semiconductor processing, e.g. photolithographic processing, performed on the epitaxial structure after semiconductor growth. For example, the SLED device can be fabricated with a narrower waveguide, which would result in a narrower horizontal mode size and higher electrical current density, the latter translating to a higher carrier density in the active region and, therefore, in a higher material and modal gain. This will, typically, result in higher electro-optical efficiency values for the SLED device. In contrast, the SOA device can be fabricated with a wider waveguide, which would result in a wider horizontal mode size and hence in a larger nonlinear Psat value and larger damage thresholds. In a ridge structure, the width of the optical mode in the waveguide, wm, can be varied by varying the ridge width wr. In a planar structure, the optical mode width, wm, can be varied by varying the width of the contact stripe electrode(s) used to inject carriers.

Example: For visible and NIR wavelengths, the ridge width 'wr' or mode width 'wm' of the SLED may be 1.0-3.5 µm, while the ridge or mode width of the SOA may be in the range 3.0-7.0 µm, with the ratio of widths between the SLED and SOA being in the range 1:6 to 1:2.

Furthermore, the SOA device may feature an asymmetric design where the ridge waveguide is narrower on the input side (i.e. towards its rear facet facing the SLED), for example it may be beneficial for coupling efficiency to match the input mode width of the SOA to the output mode width of the SLED. This can be achieved by the SOA waveguide being wider on its output side (i.e. at its front facet) than at its input side, i.e. tapering out in the forward-travelling direction. The width of the waveguide of the SOA may vary continuously and linearly from the input to the output along the length of the SOA chip, as discussed below in connection with FIG. 5, or it may also change its width only in certain sections of the SOA chip, for example a tapered waveguide design only on the input side or the output side of the SOA, as discussed below in connection with FIG. 6.

Figure 5:
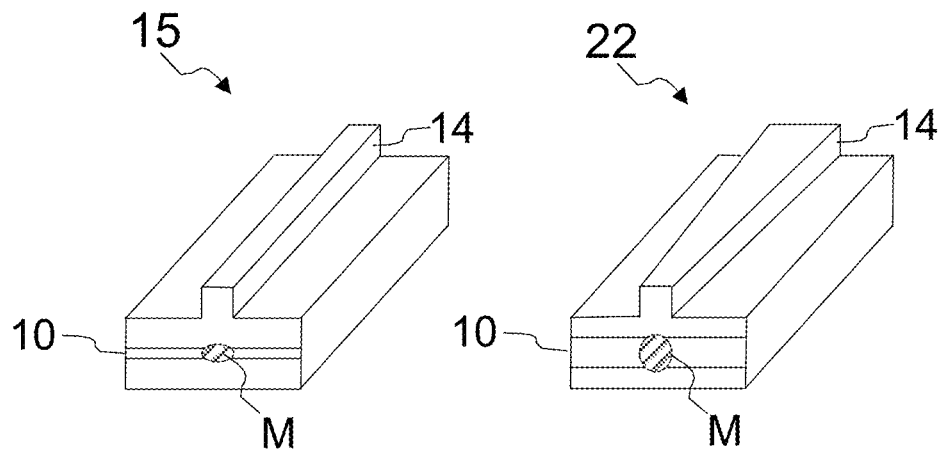
FIG. 5 is a schematic perspective drawing of another example realization of the SLED and SOA different from FIG. 2.

FIG. 5 is a schematic perspective drawing of a second example realization of the SLED and SOA. The SLED is the same as in FIG. 2, with a constant width along its length, but the SOA has a tapered ridge, where the ridge is narrowest at the input (rear) end facet and widens over the length of the chip to be widest at the output (front) facet. In particular, the width at the rear facet may be matched, e.g. set equal to, the width of the ridge at the front facet of the SLED.

Figure 6:
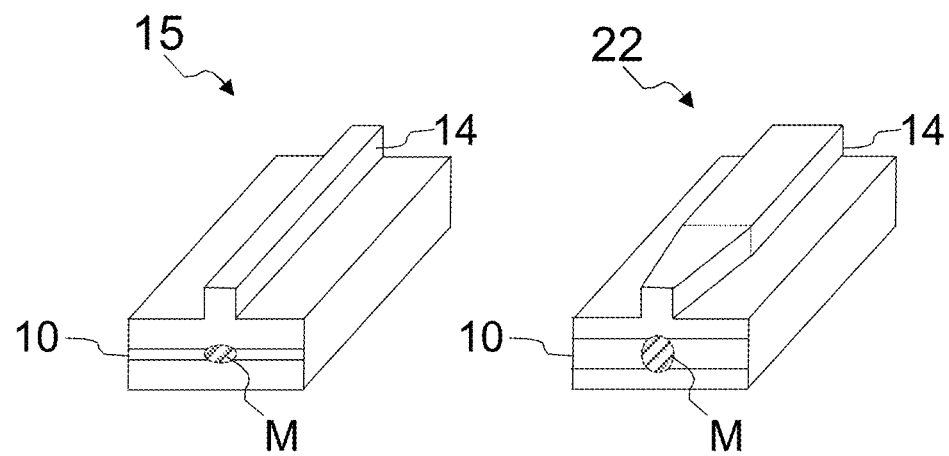
FIG. 6 is a schematic perspective drawing of a further example realization of the SLED and SOA different from FIG. 2.

FIG. 6 is a schematic perspective drawing of a third example realization of the SLED and SOA. The SLED is the same as in FIG. 2, with a constant width along its length, and the SOA has a tapered ridge as in FIG. 3, but the taper here is only over a part of the length of the chip from the SOA rear (input) facet to partway along the length of the chip, whereafter the ridge width is constant for the remainder of the chip up to the front (output) facet.

In further examples (not shown) the SLED may also have a tapered ridge design, either tapering down or up in the direction from rear to front facet, either tapered over the whole length or part length of the ridge.

We note that if the SOA or SLED chip has a waveguide which tapers along part or all of its length, then the value of the confinement factor for that chip is taken as the average (=arithmetic mean) along the active segment of the waveguide.

Figure 7:
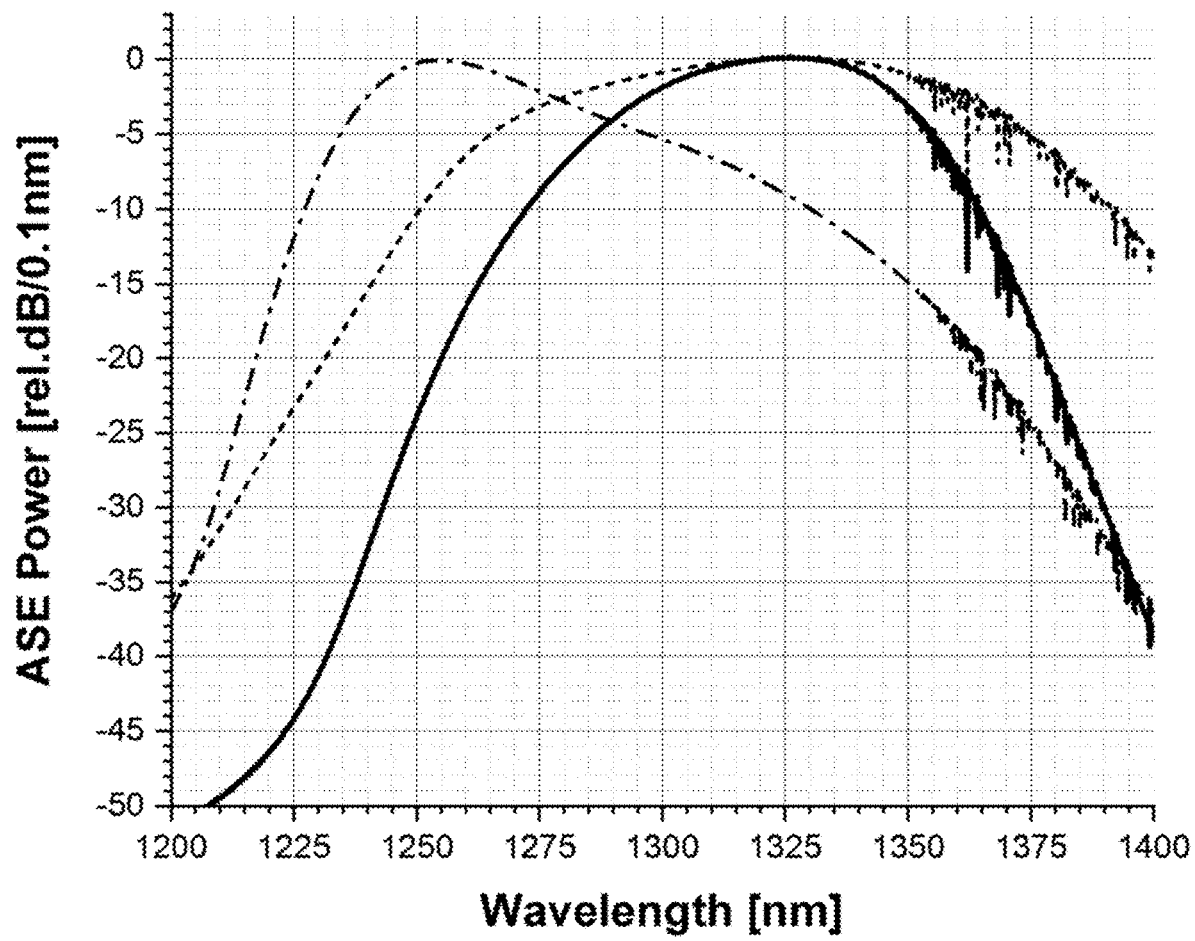
FIG. 7 is a graph showing spectral response curves of a prototype ASE source device according to an embodiment of the invention for each of the SLED component, the SOA component and the ASE source device.

FIG. 7 is a graph showing spectral response curves of a prototype ASE source device according to an embodiment of the invention for each of the SLED component (dashed line), the SOA component (dot-dashed line) and the ASE source device (solid line). The x-axis shows wavelength in nanometers and the y-axis shows power in decibels normalized to peak power which is zero dB. We discuss the wavelength ranges in terms of the 10 dB loss point, i.e. 10% of peak power. The SOA wavelength range at 10 dB is approximately 1230-1330 nm. The SLED wavelength range at 10 dB is approximately 1250-1390 nm. The combined output wavelength range is approximately 1270-1370 nm. If the center wavelengths are taken to be midway within the 10 dB output range, then these are 1320, 1280 and 1320 nm for the SLED, SOA and combined output respectively. The respective spectral bandwidths in wavelength are 140, 100 and 100 nm respectively for the SLED, SOA and combined output. The amplified ASE output from the SLED-SOA device is thus spectrally compressed compared with the SLED output (wavelength range reduced, i.e. narrowed, from 140 to 100 nm), with the compression being mainly on the short-wavelength side, but also slightly on the long-wavelength side, so that the SOA amplification produces an overall slight red shift of the SLED output (although the quoted numbers above imply no red shift). More generally, we expect the spectral bandwidth of the SLED in wavelength terms to be greater than that of the SOA by at least 10, 20 or 30%, but less than perhaps 40, 30 or 20%. There may also be a red shift of the center wavelength of the combined output compared with that of the SLED output of perhaps a few percent, e.g. 1-5%. The respective responses of the SLED and SOA may also be designed to provide a power output as a function of wavelength which is as constant as possible over the wavelength range, for example with a SLED having an ASE spectrum that has a higher power spectral density at shorter wavelengths, since it would be expected that the SOA would have lower gain at shorter wavelengths, which would thus flatten this out.

The polarization properties of the output are now discussed. Semiconductor SLED devices and SOA devices with a broad spectral gain and a spectrally-broad light output typically support only one polarization, usually the horizontal or TE polarization. This is partially because the active region is realized with single or multiple QWs which are each very thin (e.g., QW thickness values of 5 to 15 nm). For QWs of these widths the spectral gain for TE- and TM-polarized light have very different characteristics. Realizing polarization-insensitive SLED devices and SOA devices would require that the material gain and the confinement for TE- and TM-polarized light be carefully matched, which limits the design freedom over certain parameters and so may tend to limit the achievable bandwidth, output power or electro-optical efficiency. Therefore, the natural implementation of the proposed combined SLED-SOA device will be to deliver broadband light output with a single linear polarization, in particular TE polarization.

As mentioned further above, adjusting the etch depth of the ridge relative to the active region changes the relationship between the ridge width 'wr' and the fundamental mode width 'wm' induced by the ridge.

Figure 8:
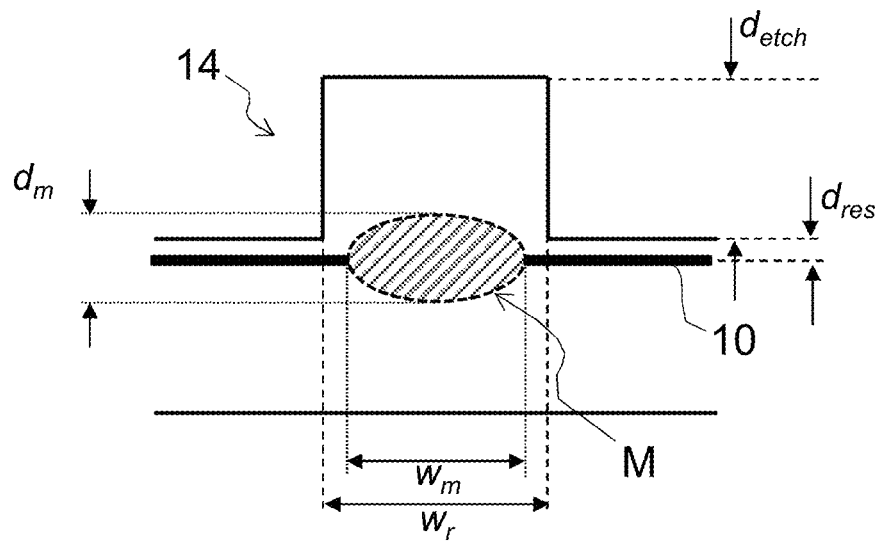
FIG. 8 is a cross-section of a SLED or SOA with a relatively deeply etched ridge.
Figure 9:
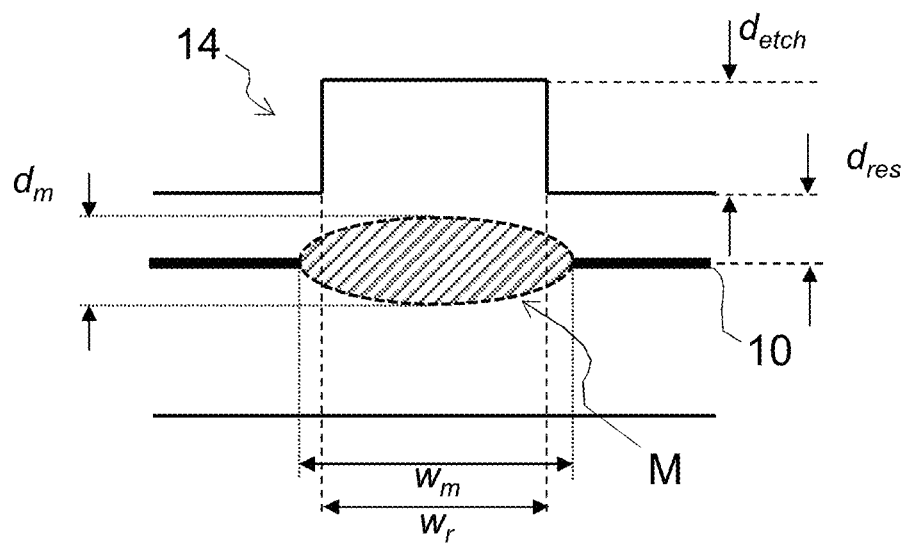
FIG. 9 is a cross-section of a SLED or SOA with a relatively shallowly etched ridge for comparison with FIG. 8.

FIG. 8 is a cross-section of a SLED or SOA with a relatively deeply etched ridge 14, whereas FIG. 9 is a cross-section of a SLED or SOA with a relatively shallowly etched ridge 14. The etch depth is marked as 'detch'. Etch depth is usually referenced to the level of the top contact or cap layer. Residual thickness is the term used to describe the depth at which the active region is buried below the etched surface of the chip is marked as 'dres'. Residual thickness is typically referenced to the middle of the active region 10. Typical values for dres are in the range of 100 nm to 350 nm. Small residual thickness values will result in a larger effective refractive index difference for the waveguiding mode in the horizontal direction, leading to potential confinement and guiding of higher-order transverse modes, so that the waveguide becomes multi-mode in the lateral direction, which depending on what is desired with a particular design may be deliberately designed out (i.e. avoided) or designed in (i.e. included). Of course, the waveguide will in nearly all cases remain single-mode in the vertical direction owing to the typical dimensions of the quantum wells. The vertical extent, i.e. thickness, of the fundamental mode 'dm' is also shown. Regarding the width of the active region, by comparing FIG. 8 and FIG. 9 it can be seen that the etch depth of the ridge 'detch' relative to the buried depth of the active region layer 'dres' affects the lateral width of the optical mode, with deeper etching (FIG. 8) resulting in the lateral mode width 'wm' becoming smaller than the physical width of the ridge 'wr' and more laterally confined, and shallower etching (FIG. 9) reversing this relationship with the optical mode laterally spreading beyond the width of the ridge and being less laterally confined. The lateral mode may therefore be wider, the same width or narrower than the ridge depending on the exact fabrication details. It will also be understood that we are implicitly discussing the fundamental mode here, since most of the power will reside in the fundamental mode. The higher order modes will be less well confined laterally compared with the fundamental mode. The width of the optical mode in the active region can also be defined with reference to, or approximated by, the width of the ridge for index-guided semiconductor devices with an etched waveguide ridge. However, this is not the case for non-ridge structures, such as gain-guided devices. In such structures, the width of the active region can be defined with reference to, or approximated by, the width of the carrier-injecting contact. The SLED and SOA could be integrated on the same chip. For example, a waveguide structure could be realized that features two separate electrical contacts, one for the ASE-generating SLED (seed) and one for the ASE-amplifying SOA (booster). The waveguide design could be substantially different in both sections, for example the SLED could feature a narrower ridge while the SOA section could feature a wider or a tapered ridge. Furthermore, the waveguide profile of both sections could also differ vertically. It can therefore be appreciated that the SLED could be realized with a shallow etch depth (FIG. 9) to reduce the lateral confinement for unwanted higher-order waveguide modes, while the SOA could be realized with a deeper etch depth (FIG. 8) to reduce lateral current spreading and to improve waveguiding in a wider-ridge structure.

Figures 10A, 10B:
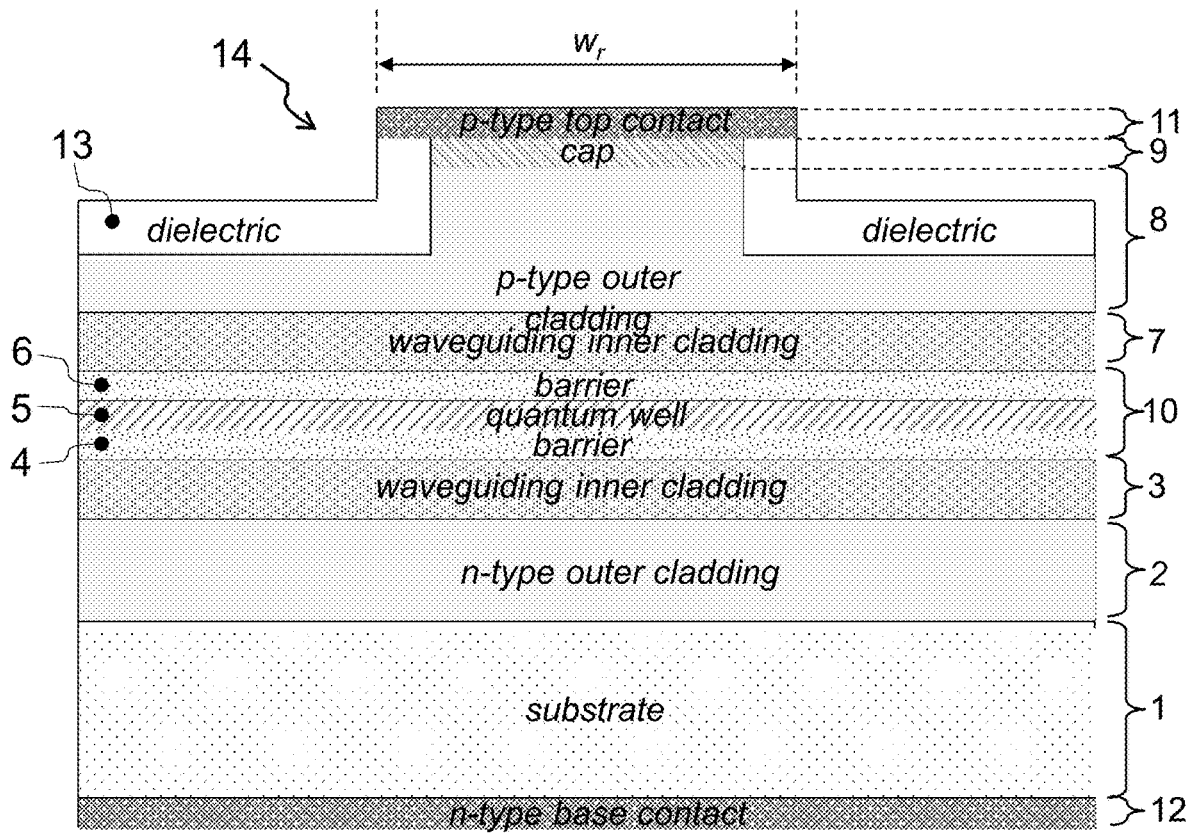
FIG. 10A is a schematic cross-section showing an example layer structure of a SLED or SOA embodying the invention.
FIG. 10B is a table showing example materials choices for SLED or SOA fabrication in each of four different materials systems.

FIG. 10A is a schematic cross-section showing an example layer structure of a SLED or SOA embodying the invention in more detail than FIG. 3 or FIG. 4. The semiconductor epitaxial layers are arranged on a substrate 1, the epitaxial layers from the substrate 1 up being: lower outer cladding layer 2, lower inner cladding layer 3, active regions layers 4, 5 and 6 (collectively labelled as 10), upper inner cladding layer 7, upper outer cladding layer 8, and cap layer 9. The active region layers 4, 5, 6 are of higher refractive index than the inner cladding layers 3, 7, which are in turn of higher refractive index than the outer cladding layers 2, 8. In terms of carriers, the outer cladding layers 2, 8 are respectively doped n-type and p-type (or vice versa) to enable carrier injection across the active region layer(s) 10. The active region layers 4, 5, 6 form a QW structure, with a well layer 5 sandwiched between lower and upper barrier layers 4 and 6. If the active region includes multiple QWs, then this layer structure will be repeated for each QW. Each well hosts, in operation, a reservoir of carriers that are available for spontaneous emission, the well having a suitable band gap (or band gaps) for providing the amplification. The ridge 14 is formed after growth of the epitaxial structure by etching away the cap layer 9 and a part of the outer cladding layer 8. A dielectric layer 13 is then deposited to cover the surface of the outer cladding layer 13. A top contact layer 11 is deposited on the top of the ridge 14 over the cap layer 9, and a base contact layer 12 is deposited on the underside of the substrate 1, the contacts serving as electrodes to allow the drive current to be applied across the active region 10. It will be appreciated that each of the illustrated layers may be made of multiple layers. Moreover, other structures are possible, e.g. with graded refractive index designs.

Regarding the thickness of the active region 10, this is principally defined by the thickness of the waveguide core between the waveguide cladding, the core being formed by the QW region and the cladding being formed by the inner cladding layers. We define the active region thickness in this document as either the sum of the thicknesses of the layers 4, 5, 6 between the lower and upper waveguide cladding layers 3 and 7, or the distance between the bottom of the upper cladding layer 7 and the top of the lower cladding layer 3. In a typical implementation using a single QW or multiple QWs made up of one or more QW layers and corresponding barrier layers, the active region thickness will be the sum of the thicknesses of the well and barrier layers, possibly including any additional layers that may be present between the (M)QW structure and the waveguide cladding layers. Another alternative is to have an active region without quantum wells, i.e. based on a conventional pn-junction across a bulk, i.e. 3D, band gap.

FIG. 10B is a table summarising material choice options for the different epitaxial layers for each of four known materials systems for fabricating SLEDs, which are also suitable for fabricating SOAs as proposed in this document. In the left-hand column: the label 'cladding' corresponds to the outer cladding layers 2, 8; and 'waveguide' the inner cladding layers 3, 7. The principal materials systems of choice for fabricating SLEDs, as set out from left to right in the table are GaAlInN (sometimes referred to as GaN-based or nitride-based) for the wavelength range 390-570 nm, GaAlAs (sometimes referred to as arsenide-based) for the wavelength range 570-1150 nm, GaAlInP (sometimes referred to as phosphide-based) for the wavelength range 1150-2000 nm, and GaAlInAsSb (sometimes referred to as antimonide-based) for the wavelength range 2000-2700 nm. The SOAs proposed in this disclosure can also be fabricated with the same materials system choices. For current commercial SLEDs in the visible and near infrared (NIR) ranges, phosphide- and arsenide-based systems are predominantly used for red wavelengths and nitride-based systems for blue and green wavelengths. The same will apply for the SOAs proposed in this disclosure.

The wavelength range of an individual SLED or SOA is defined by a variety of design parameters including its epitaxial semiconductor stack structure and materials, the dimensions of the ridge in the case of a ridge structure, and the properties of the chip's end facets. The wavelength range may have a value between 3 nm and 160 nm at full width half maximum (FWHM), i.e. 3 dB attenuation level. It is the case that, for comparable designs, the FWHM scales with the square of wavelength, so the maximum possible wavelength range for comparable designs increases for longer wavelengths. With future developments in technology it may be possible to broaden the maximum wavelength range at any particular center wavelength. The wavelength range covered by an individual SLED or SOA as disclosed herein may have any value between 3 nm and 160 nm. With current technology and using the arsenide- and phosphide-based materials system wavelength ranges up to about 160 nm are achievable in SLEDs or SOAs with center wavelengths in the near infrared (NIR) and infrared (IR). With current technology and using the nitride-based materials system wavelength ranges up to 30 nm are achievable in blue and green SLEDs or SOAs. For example, the wavelength range may have a value of 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 110, 120, 130, 140 or 150 nm.

Figure 11:
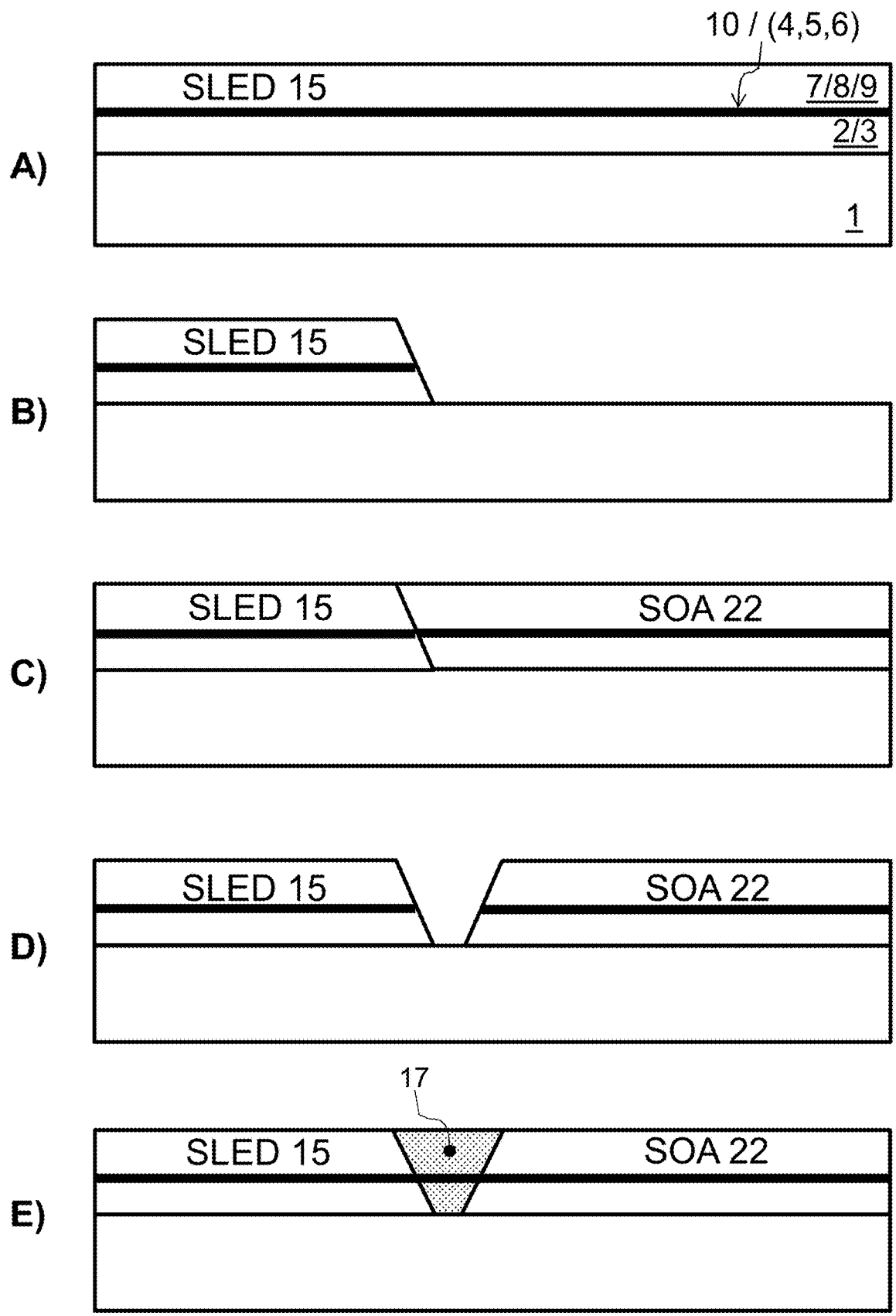
FIG. 11 shows a series of schematic wafer cross-sections during fabrication of an integrated ASE source device embodying the invention.

FIG. 11 shows in schematic cross-section an example wafer at steps A to E in the fabrication of an integrated ASE source device embodying the invention. Each of the schematics A to E is a schematic cross-section of a portion of a semiconductor wafer.

In Step A, the epitaxial layers 2 to 9 for the SLED 15 are blanket deposited on a substrate 1, i.e. over the entire wafer.

In Step B, the epitaxial layers 2 to 9 are then removed from one side of the device area by lithographic patterning and etching. Here it is noted that the SLED and SOA may share common specifications for some of the layers, e.g. the lower outer cladding layer 2 and perhaps also the lower inner cladding layer 3, so the etching away, or other removal, of the SLED epitaxial layers may leave common layers in place. (Alternatively, Step A could be omitted and Step B involve depositing layers 2 to 9 over a part of the wafer, with the other part being masked off.)

In Step C, epitaxial layers 2 to 9 for the SOA 22 are deposited alongside the SLED structure, the latter being masked.

What is shown in Step C could represent the end of the growth process.

Optionally, the growth process may continue as shown in Step D by removal of the epitaxial layer material along a V-shaped channel 17 (extending perpendicular to the plane of the paper).

What is shown in Step D could represent the end of the growth process, with the SLED output facet being optically connected to the SOA input facet by microbonding of suitable optical elements in between.

Optionally the growth process may continue as shown in Step E by performing overgrowth in the channel to form a passive waveguide section that bridges between the SLED and SOA active regions, the core material of the passive waveguide section having a larger bandgap than the short-wavelength end of the wavelength range of the SLED output such that the passive waveguide section is transparent and passive, i.e. non-amplifying and free of non-linear effects, for light transferring from the SLED to the SOA. The structure shown in caption E thus provides the basis for fabricating monolithically integrated ASE source devices with a serially connected SLEDs and SOAs once the post-growth fabrication steps, e.g. ridge formation and contact formation, are completed.

After the fabrication steps shown schematically in FIG. 11, the wafer would then undergo standard wafer processing with photolithographic masks to form the actual waveguide structures, e.g. the ridge in case of a ridge waveguide embodiment, and other features required for the SLED and SOA sections.

We now describe in more detail various possible designs for the SLEDs that may be used in embodiments of the invention.

Standard SLED devices are designed to operate in a regime of amplification of the spontaneous emission without reaching lasing operation.

The output power from the front facet side of a SLED at a given current can be written as:

$$Pout \sim Ps \cdot \frac{1 + G_0(L) \cdot R_b}{1 - G_0^2(L) \cdot R_b \cdot R_f} \cdot (G_0(L) - 1) \cdot (1 - R_f)$$

where Ps is the spontaneous emission power coupled into the propagating optical mode, Rb and Rf are the back and the front facet reflectivities and $G_0(L)$ is the SLED single pass gain:

$$G_0(L) = \exp((\Gamma g - \alpha_i) \cdot L)$$

where $\Gamma$ is the modal confinement factor, g the peak material gain, $\alpha_i$ the internal loss, and L the chip waveguide length.

For a SLED to operate in a light amplification regime without achieving lasing the following conditions must be satisfied:

$\Gamma g > \alpha_i$ (amplified spontaneous emission regime)

$G_0^2(L) \cdot R_b \cdot R_f << 1$ (lasing condition is reached at unity)

The conditions needed to suppress lasing can be achieved by appropriate design of the cavity. In particular, it is important to avoid undesired multiple passes through the cavity, which can be supported by avoiding light backscattered from the end facets, e.g. by reflection, coupling back into the SLED waveguides.

When both facet reflectivities are negligible (Rf=Rb≈0) $P_{out}$ becomes:

$$Pout \sim Ps \cdot (G_0(L) - 1)$$

In this case, the SLED design is called a single-pass design.

When the back-facet is highly reflective (e.g. Rb≈100%) and the front-facet reflectivity is negligible ((Rf≈0;) Pout becomes:

$$Pout \sim Ps \cdot (G_0^2(L) - 1)$$

In this case the SLED design is called double-pass design.

The output facet reflection losses can be increased by implementing the following elements/solutions in the SLED chip design:
  a) antireflection coatings
  b) tilted waveguides
  c) part-curved waveguides
  d) passive absorber sections Combinations of any of these measures are also possible. Some examples of implementing one or more of these options are now described in more detail.

The gain section is electrically injected with carriers via injection electrodes. Light is thus generated and then amplified as it travels along the waveguide. The passive absorber section shares with the gain section the same epitaxial layer sequence (p- and n-layers; active region layers) and is geometrically defined on the chip during the device fabrication process. The passive absorber section may share with the gain section a ridge waveguide structure or not. Embodiments with no ridge waveguide in the absorber section can be realized by blanket etching over the absorber section during the fabrication process to remove the material which elsewhere forms the ridge. In contrast to the gain section, the passive absorber section is not electrically injected, its purpose being to absorb light and prevent the guided optical radiation to reach the back facet and being coupled again into the gain section. In the case of the absorber section sharing a ridge waveguide with the gain section, the waveguide part falling in the absorber section may also share with the gain section the electrical isolation layer and may include a top metallic contact layer which is electrically separated and independent from the top metallic contact layer in the gain section. In the case of the passive absorber section sharing a ridge waveguide with the gain section and implementing a top metallic contact layer, the absorber top contact layer may be electrically floating, connected to ground or maintained in reverse bias during operation.

For the SOA design, many of the detail design considerations are similar to the SLED design considerations discussed above. However, there are differences of principal based on their respective functions.

The SLED is intended to operate as a broadband ASE source, which means that it should be optimized to output from its front facet a broadband beam with high overall power, relatively even power across its emission spectrum (e.g. low ripple and no significant spikes), and with high electrooptic efficiency (e.g. as measured by wall plug efficiency), as well as being optimized so that back-reflections or back-scattering from the back facet are suppressed as much as possible, for example by introducing absorber sections.

The SOA on the other hand has the function of amplifying the broadband signal it receives from the SLED, typically only at a certain polarization, and to output a reasonably faithfully amplified copy of the SLED output signal at its output, although predictable transformation of the SLED signal are acceptable, such as a certain amount of spectral narrowing or an increasing gain with wavelength across the amplified wavelength range. Another design factor specifically relevant for the SOA is an optimization for a low noise figure (NF), because the role of the SOA is to amplify its input signal, not to act as an ASE source, since any ASE within the SOA may add unwanted noise power in the background which will be amplified and represent noise on top of the amplified SLED signal. To keep the NF low, the coupling efficiency on the input side of the SOA should be maximized and the self-generation of ASE in the SOA minimized while keeping the signal gain at a reasonable level. Following those device requirements, the SOA is optimally implemented with a low-confinement structure such that the self-generated ASE output power is rather low, wherein the consequent reduction in modal gain can be compensated for by increasing the length of the SOA. It is therefore to be expected that the SOA chip length is greater than the active segment length of the SLED chip, noting that in the SOA the whole chip will typically be one active segment. For example, a SLED chip may have an active segment length between 400 µm and 1300 µm, while the SOA with which it is paired may have a chip length (=active segment length) in the range of 1300 µm to 2000 µm. The SOA chip may require a longer length because of the lower confinement, the latter being chosen to provide a low NF value and a high Psat value. For the SOA design, it is also desirable to have high facet reflection losses as for the SLED to ensure single-pass operation, to avoid a resonant cavity being formed, and to suppress any back-coupling of light from the SOA into the SLED. To achieve this, the SOA may beneficially have antireflection coatings on at least one, preferably both, end facets and may incorporate a tilted waveguide design as mentioned above for the SLED design. The SOA could also incorporate a part-curved waveguide, although this would reduce output power.

Figure 12A:
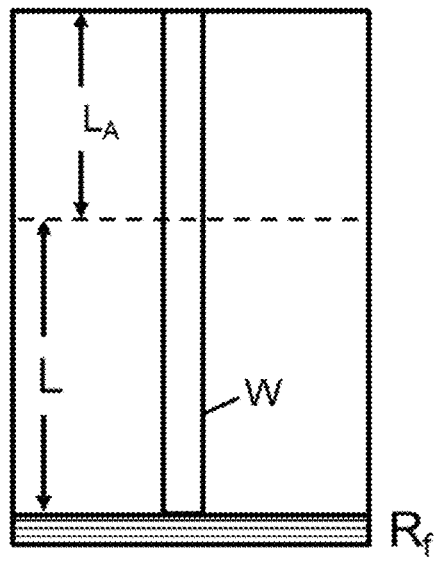
FIG. 12A is a schematic plan view of a first example SLED designed.

FIG. 12A is a schematic plan view of a first example SLED designed for single pass with a straight ridge waveguide W extending perpendicular to the end facets of the chip and over the full length of the chip from back facet to front facet, and a passive absorber which includes a portion of the ridge.

Figure 12B:
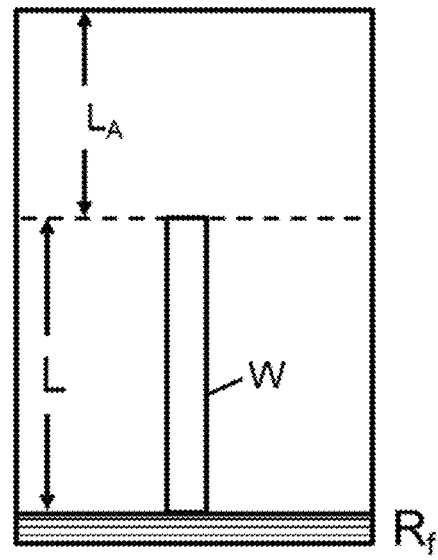
FIG. 12B is a schematic plan view of a second example SLED.

FIG. 12B is a schematic plan view of a second example SLED designed for single pass with a straight ridge waveguide W extending perpendicular to the end facets of the chip and over a distance L covering a first part of the length of the chip from the front facet to part way towards the back facet and a passive absorber extending over a distance LA covering a second part of the length of the chip from the chip interior end of the waveguide to the back facet. In the design of FIG. 12B, the cavity's optical path between the front and back facets is thus partly through the waveguide and partly outside the waveguide in contrast to the design of FIG. 12A in which the cavity's optical path is entirely within the waveguide.

Figure 12C:
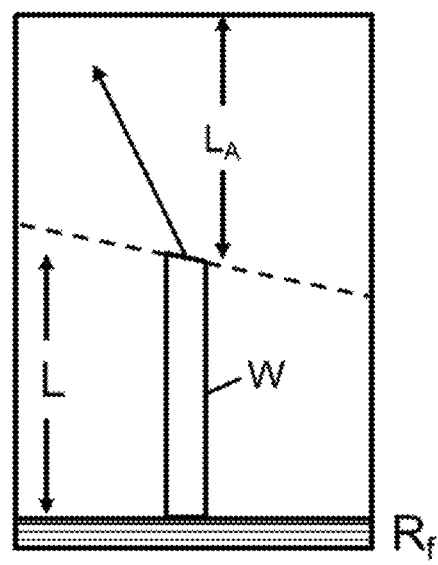
FIG. 12C is a schematic plan view of a third example SLED.

FIG. 12C is a schematic plan view of a third example SLED designed for single pass similar to FIG. 12B, but with the chip interior end of the waveguide terminating at a tilt proximal to its interface with the passive absorber, wherein the tilt serves to further suppress reflections from the back facet of the chip being coupled back into the waveguide.

FIGS. 12A, 12B and 12C are examples of single-pass designs in which both facet reflectivities are negligible, i.e. kept as low as possible, and the light is amplified along the waveguide on a single pass. These examples also have in common that the ridge and hence the underlying waveguide W is straight. Back-reflection from the back is suppressed by introducing a passive absorber section of length LA in the chip design. Length L is the length over which the chip is driven to inject carriers with suitable drive electrodes, whereas length LA is the length over which the chip is unbiased or reverse biased with suitable biasing electrodes to support the function of the passive absorber material. The ridge and hence the waveguide may or may not (see FIG. 12A and FIG. 12B respectively) extend over the passive absorber section. The passive absorber section is not subject to electrical carrier injection and should not reach transparency, i.e. photobleaching should be avoided, since otherwise the absorption function of the passive absorber section will be compromised. The passive absorber section absorbs unwanted light travelling backwards in the chip after reflection from the back facet. In the case of a passive absorber without a ridge waveguiding structure, like that of FIG. 12B, the boundary interface (dashed line) between the active waveguiding section and the passive absorber section can be made tilted to further reduce possible reflections at the back facet as shown in FIG. 12C. Here the light emitted from the waveguide into the passive absorber section is emitted at an angle from the waveguide as a result of the tilt. The front facet is covered with a dielectric coating having low reflectivity Rf, i.e. an anti-reflection coating (ARC), in order to suppress light feedback from the front facet from which the light is output.

Figure 12D:
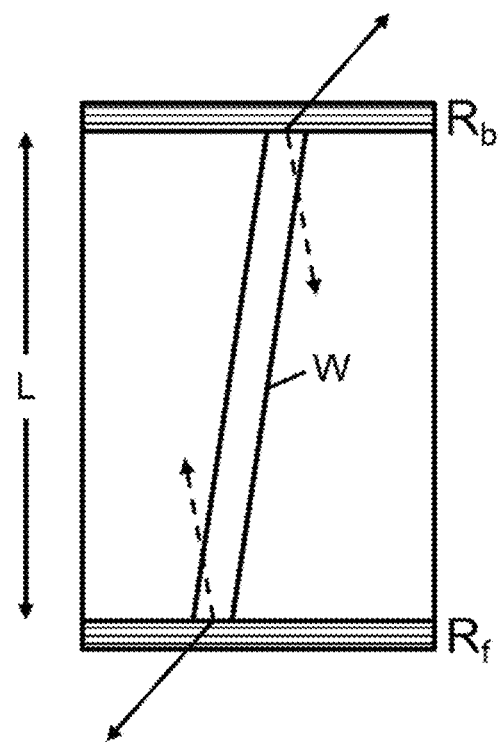
FIG. 12D is a schematic plan view of a fourth example SLED.

FIG. 12D is a schematic plan view of a fourth example SLED designed for single pass with a straight ridge waveguide extending tilted at an angle over the full distance between the end facets of the chip. The tilt angle 't' is less than the critical angle for total internal reflection, e.g. $0<t\leq 25°$, since otherwise the output would not be possible. Solid arrows show the output direction, noting that there is output from both end facets of the chip. Dashed arrows show the direction of internal reflections, which it can be seen are lost from the waveguide and so will not result in multipass traversals between the facets which could induce lasing. The amount of reflected light at the end faces which is coupled back into the SLED chip can be further reduced by applying AR coatings on at least one, preferably both, of the end faces. Both facet reflectivities Rf, Rb are made as low as possible and the light is amplified along the waveguide in a single pass. A variant of this design would be to incorporate an absorber section towards the rear/back facet as in the previous examples.

Figure 12E:
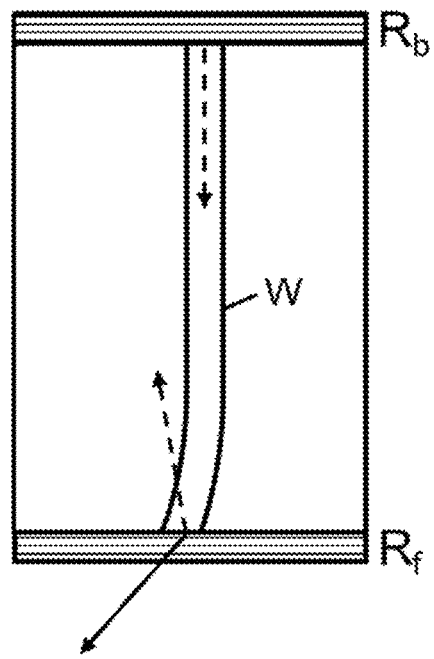
FIG. 12E is a schematic plan view of a fifth example SLED.

FIG. 12E is a schematic plan view of a fifth example SLED designed for double pass with a ridge waveguide which has a straight portion extending perpendicular to the end facets of the chip from the back facet to some distance away from the front facet and a curved portion extending over the remaining distance to the front facet so that the ridge waveguide meets the front facet at a tilt angle 't' away from perpendicular which is less than the critical angle for total internal reflection from the front facet, e.g. $0<t\leq 25°$. The critical angle is a function of the material. For example, GaN has a critical angle approximately 24°; GaAs and InP have a critical angle approximately 15° to 17°. Alloys of these materials have other values. With a double-pass design of this kind, the back-facet reflectivity cannot be neglected. The light propagating towards the back direction is amplified once and then, after undergoing reflection at the back facet, undergoes further amplification when travelling towards the front facet. The SLED chip has a ridge waveguide W which has a straight section extending from the back facet (which is reflective to achieve double pass) and a curved section extending from the front facet (where the output occurs) so that the curve results in the waveguide intersecting with the front facet at a non-perpendicular, tilted angle, i.e. with a non-normal incidence. The back, reflecting facet has a high reflection (HR) coating to maximize the amount of light reflected back into the waveguide at the back facet of the chip. The amount of light coupled back into the SLED cavity at the front facet is suppressed by the waveguide meeting the front facet at an angle, this tilt angle away from perpendicular being e.g. $0<t\leq 25°$. The onset of lasing can be further shifted by providing an AR coating on the front facet.

The above discussion of the single-pass SLED design options with reference to FIGS. 12A to 12D is applicable also to the SOA design options. (The double-pass design of FIG. 12E is not suitable for the SOA.)

We now describe, from a packaged, construction point of view several embodiments of modules incorporating ASE source devices based on serially connected SLEDs and SOAs according to embodiments of the invention. These are all illustrated using SLEDs and SOAs with a single-pass, straight, tilted ridge waveguide as described above in relation to FIG. 12D. However, it will be understood that all the following embodiments could be varied by using any of the other above-described suitable types of SLED and SOA instead.

In the embodiments described herein, it will be recognized that the SLEDs and SOAs are based on edge-emitting structures, mainly with ridges, but also ridgeless with the lateral confinement defined by the injection electrode widths.

Figure 13:
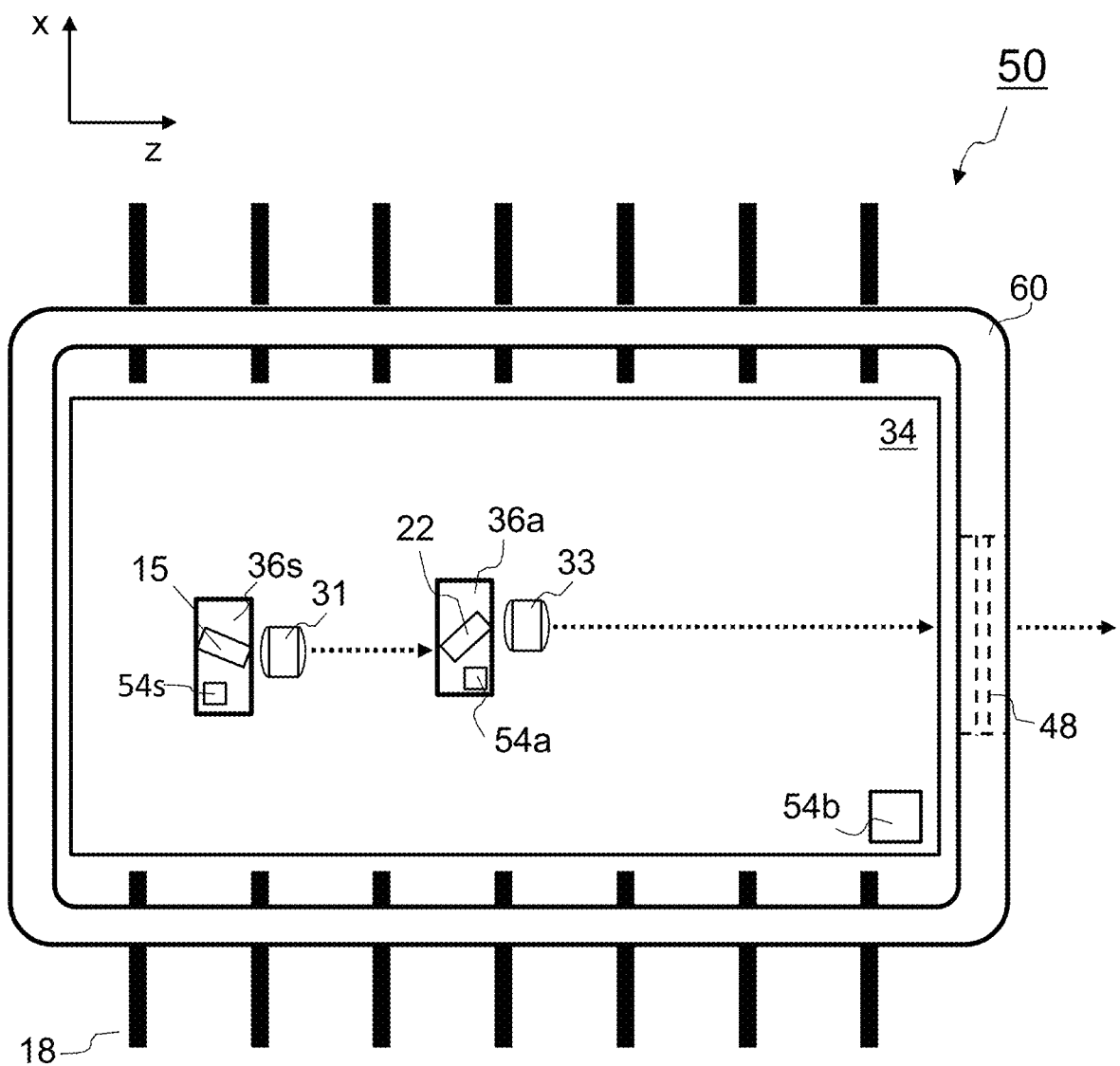
FIG. 13 is a schematic plan view of an ASE source module according to a first embodiment.

FIG. 13 is a schematic plan view of a combined SLED and SOA source module according to a first embodiment with free-space output. The module is based on a butterfly package 50, shown as a 14-pin butterfly package. The butterfly package 50 has a plurality of terminal pins 18 via which electrical connections may be made to components housed in the package. The butterfly package 50 has a housing 60 that forms an enclosure in which a SLED 15 and a SOA 22 are accommodated as well as associated components. The components are at least for the most part mounted directly or indirectly on a main board 34, which may also be referred to as a carrier board, substrate, optical breadboard or mounting board. The main board 34 is provided with a temperature sensor 54b arranged on the main board 34 to measure the temperature of the main board. The main board 34 should have good thermal conductivity for heat dissipation, and should be mechanically stiff. Suitable materials choices are ceramic, e.g. AlN or Al2O3, a suitable metal, e.g. copper, aluminium or alloys containing either or both of these metals such as CuW. The upper and/or lower surface of the main board 34 may be metallized to support solder processes for the attachment of the components, in particular for electrical connections. Metallization may also aid good thermal connection to cooling elements for maintaining the temperature inside the enclosure within a specified range. For physical attachment of components by bonding, e.g. with epoxy resin, the upper and/or lower surfaces of the main board 34, or selected areas thereof, may be specified with a minimum surface roughness to provide good adhesion.

The housing 60 and the enclosure it defines by its internal walls are substantially rectangular in plan view as illustrated aligned with orthogonal axes x and z respectively across and along the module as illustrated, with y being the axis out of the paper, i.e. the vertical. The module has its optical output port arranged at one end of the enclosure in an end wall of the housing 60. The optical output port comprises a window 48 arranged in the end wall of the housing 60 to allow the combined beam to be output from the housing in the z-direction. It will be appreciated that the module also has a lid (not shown) which may be secured removably or non-removably to the housing by fasteners, such as screws or rivets, and/or adhesive bonding, welding or other fastening or sealing means as desired.

The SLED 15 and the SOA 22 are mounted on respective submounts 36, labelled 36s for the SLED 15, and 36a for the SOA 22. The submounts 36 are, in turn, mounted on the main board 34. The materials choices for the submounting boards 36 are similar to those as described above for the main board 34. The mode of assembly with populated submounts on a main board is referred to as a chip-on-submount (CoS) in the art. The SLED chip 15 and the SOA chip 22 are schematically shown mounted at an angle to their submounts 36s/a and the sides of the rectangular enclosure as would be the case for a tilted, single-pass SLED 15 and a corresponding tilted, single-pass SOA 22, in which the ridge waveguide of the SLED and SOA is tilted as a way of hindering reflections from the chip end facets. For the SLED 15 in particular it is important to minimize reflections from the back facet that may couple back into the ridge waveguide, thereby to suppress lasing action in the SLED 15. Typically, the reflectivity of both chip end facets of the SLED 15 and SOA 22 is kept as low as possible. In the SLED 15 and SOA 22, the ridge and hence the underlying waveguide 'W' may be straight or incorporate a curved portion. Back-reflection inside the SLED 15 may be further suppressed by introducing a passive absorber section. The choice of SLED type is flexible, e.g. double-pass designs with the back facet having a high reflectivity could be used. The submounts 36 may also have respective temperature sensors 54 mounted on them, labelled 54s for the SLED submount 36s, and 54a for the SOA submount 36a. These temperature sensors allow the temperature local to the SLED 15 and SOA 22 to be monitored. The temperature sensors 54b/s/a may have their signals used as control inputs for one or more cooling elements (not shown). For example the mounting board 34 may have attached to its upper or lower surface a thermoelectric cooler, e.g. a Peltier device. The submounts 36s/a may also have individual cooling elements (not shown) that can be independently controlled via the respective temperature measurements from sensors 54s/a. Light emitted from the SLED 15 is emitted in the z-direction and focused by a lens 31 onto an input area on the rear facet of the SOA 22. Light emitted from the SOA 22 is emitted in the z-direction and collimated by a lens 33 so as to be emitted as a collimated output beam from the module through the window 48. (Alternatively, if desired, the lens 33 may be configured and arranged to focus the output beam at a point outside the module.) Optionally, a polarization filter may be placed in the output beam path, e.g. after the collimating lens 33, to increase the polarization extinction ratio (PER) of the outputted beam. This may be useful when the module is specified to have a high PER, e.g. at least 20-30 dB, whereas the intrinsic PER of the SLED and/or SOA may be lower, e.g. only 3-10 dB.

Figure 14:
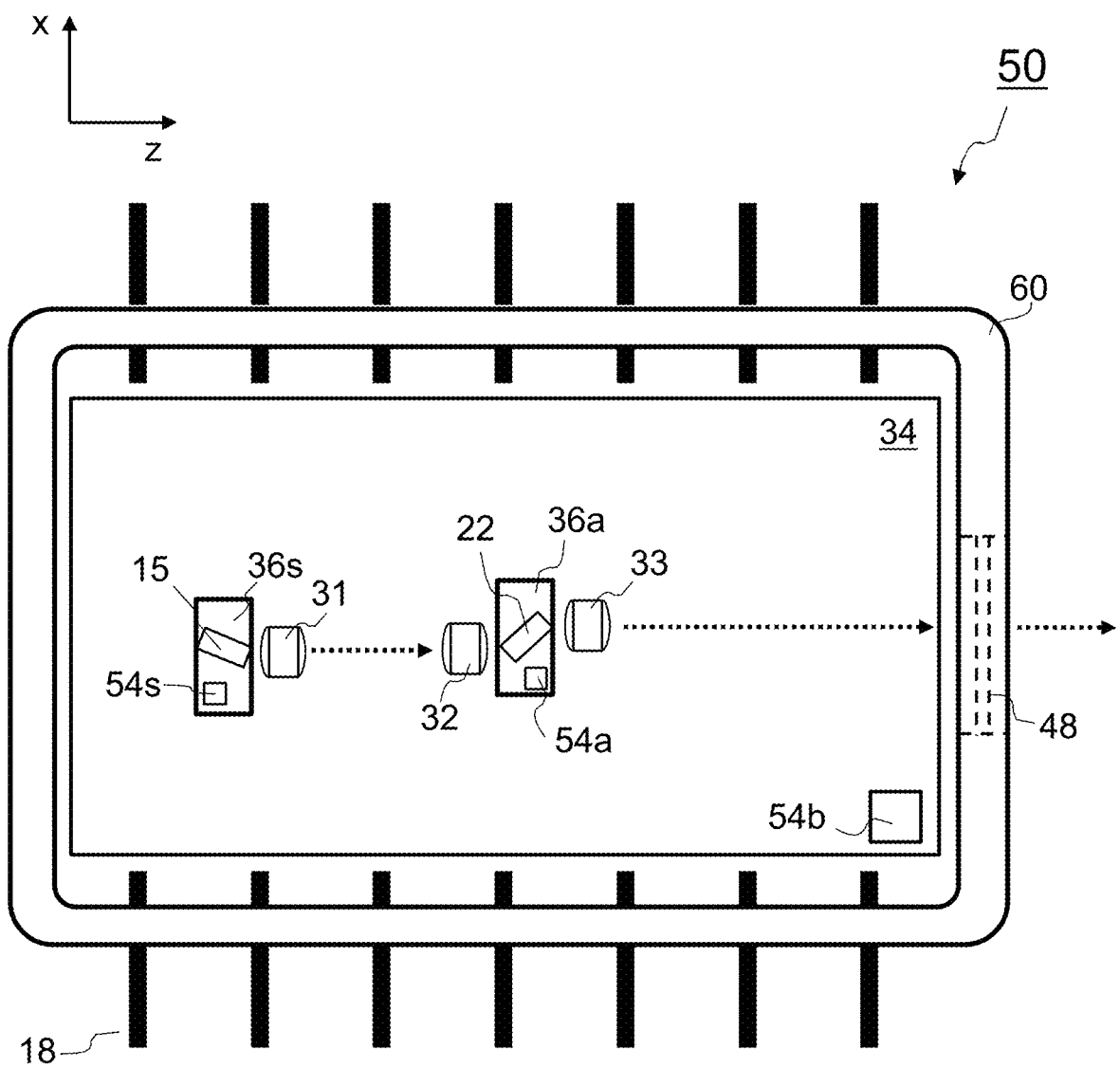
FIG. 14 is a schematic plan view of an ASE source module according to a second embodiment.

FIG. 14 is a schematic plan view of a combined SLED and SOA source module according to a second embodiment. The second embodiment differs from the first embodiment only in that the light path between the SLED 15 and SOA 22 is managed by a pair of lenses 31 and 32 (instead of a single lens), with the light beam in between lenses 31 and 32 being collimated.

Figure 15:
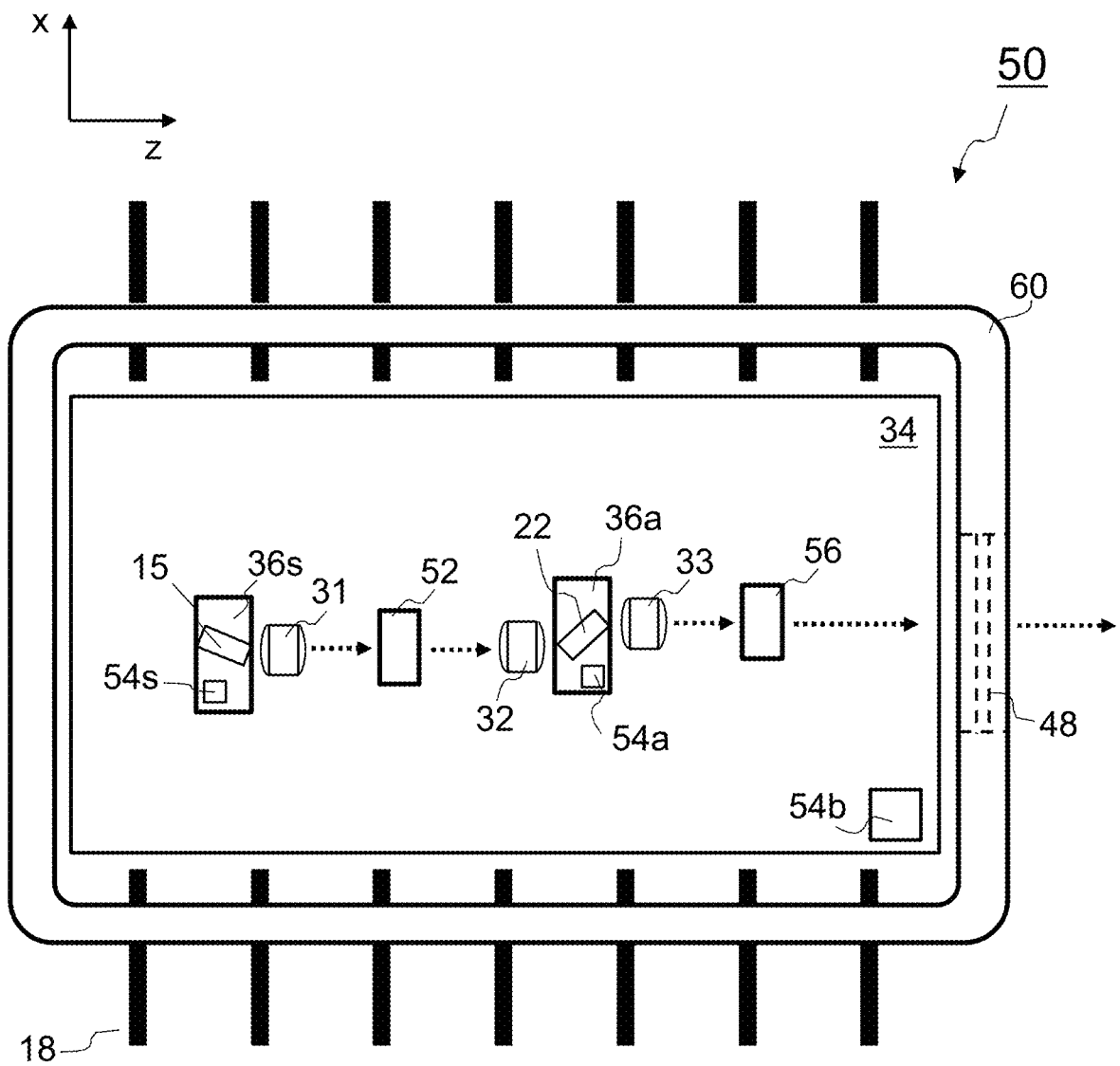
FIG. 15 is a schematic plan view of an ASE source module according to a third embodiment.

FIG. 15 is a schematic plan view of a combined SLED and SOA source module according to a third embodiment. The third embodiment is the same as the second embodiment except that additional components 52 and 56 are arranged in the beam path of the beam output from the SLED 15 and SOA 22 respectively. The components 52 and 56 may be optical isolators, optical attenuators or polarizing elements. One or both of the components 52 and 56 may be provided.

Arranging an optical isolator or optical attenuator 52 between the SLED and SOA devices 12 and 22 may help support stable operation for lower output powers. The difference between an optical attenuator and an optical isolator is that an isolator has a highly asymmetric insertion loss (IL) profile, for example it could have an insertion loss of 1-3 dB in forward direction and an insertion loss of 20-50 dB in backward direction, whereas the insertion loss of an optical attenuator is the same forwards and backwards. The function of the optical isolator (or attenuator) is to block (or attenuate) unwanted backward-travelling ASE light from the SOA from entering the SLED, which, if unchecked, could reduce the carrier density in the SLED, which would have the same effect as reducing the electrical injection current into the SLED. This may therefore cause instability and a reduction of the SLED's output power as well as a reduction of the SLED's spectral bandwidth. If unblocked or incompletely blocked, the presence of backward-travelling ASE light from the booster SOA can be compensated for by intentionally operating the SLED at an increased drive current providing that operation is still stable. However, for certain applications or systems, it might be preferable to reduce the effect of any backward-travelling ASE light from the booster SOA. Considering the forward-travelling light, using an optical attenuator as component 52 will also mean that the SLED must be driven at higher output powers, which may assist stability.

While an optical isolator is preferable in principle to an optical attenuator, small and compact optical isolators based on thin films are currently only commercially available for wavelengths above about 1000 nm, so that for shorter wavelengths optical attenuators may be preferred.

Another option to suppress unwanted backward-travelling ASE light from the SOA entering the SLED is for component 52 to be a linear polarization filter, e.g., with the filter having high transmissivity for horizontal (TE) polarization and high isolation for vertical (TM) polarization. As already outlined, in certain embodiments both the SLED and the SOA are optimized for broadband light emission and light amplification for the horizontal TE polarization. Nevertheless, both the SLED and SOA are likely to emit a residual amount of ASE light in the orthogonal TM polarization. A linear polarization filter as element 52 would then filter out the TM-polarized light emitted from the SLED in the forward direction such that the light entering the SOA has a high PER with negligible optical power in the vertical polarization axis. The light amplification in the SOA will cause carrier depletion, which causes gain compression, but the reduction of the TE gain will be stronger compared to the reduction of the TM gain. This means that any unwanted residual ASE light traveling backwards from the SOA towards the SLED is TM-polarized, and this polarization will be blocked by the linear polarization filter 52, thereby acting as a stabilising influence for the SLED source.

An optical isolator 56 arranged after the SOA 22 will serve to block backward-travelling light from arbitrary downstream optical components from entering the SOA 22, and so avoid the possibility of any resultant instability or undesired modification of the SOA's operation. An optical attenuater 56 arranged after the SOA 22 would force the SLED to be driven with a higher current and hence higher output power, which may improve its stability.

Figure 16:
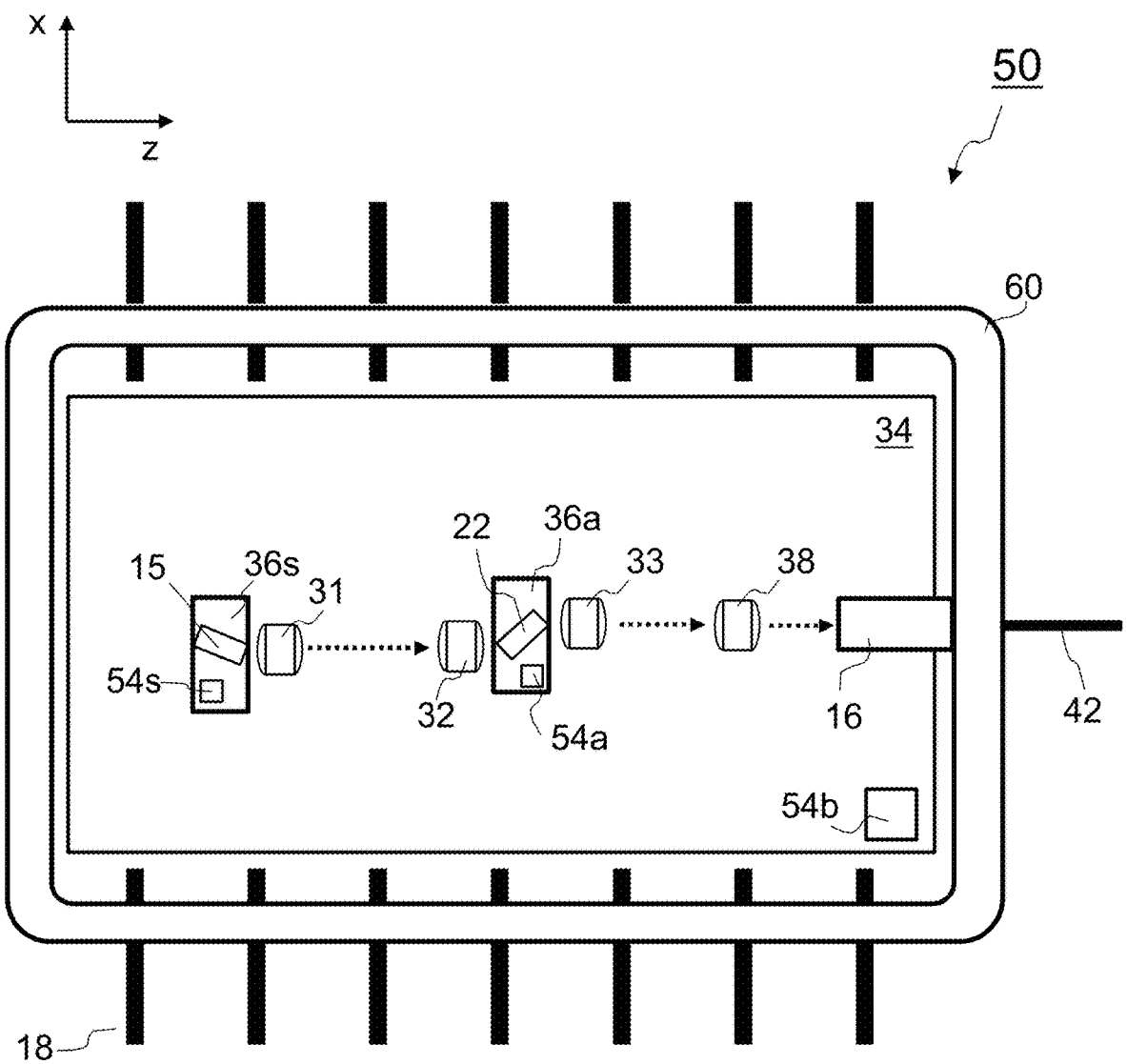
FIG. 16 is a schematic plan view of an ASE source module according to a fourth embodiment.

FIG. 16 is a schematic plan view of a combined SLED and SOA source module according to a fourth embodiment. The fourth embodiment is similar to the second embodiment, but replaces the free-space output through a window with an optical fibre output. Namely, the optical output port in this embodiment is realized with optical fibre in the form of an optical fibre ferrule 16, which is attached to an optical fibre 42 that may be single mode or multimode and may be polarization maintaining (or not) as desired. The ferrule 16 and fibre 42 form a so-called pigtail and serve to couple the output beam from the SOA 22 into the end of the optical fibre 42 and thus out of the module 5. The fibre ferrule 16 may also be attached to the main board 34, or may be secured to the housing 60, e.g. to the end wall. It is further noted that the light output from the SOA 22 is focused onto the fibre end via two lenses 33 and 38. In other embodiments, a single lens could be used.

The modules described above consist of a single SLED and SOA. However, further modules may usefully combine multiple SLED/SOA pairs.

As mentioned further above when discussing the polarization properties of the output beam, the natural implementation of the proposed combined SLED-SOA device will be to deliver broadband light output with a single linear polarization, in particular TE polarization. This means that two or more SLED-SOA devices with the same spectral characteristics may be combined using polarization multiplexing in a single module. By the same, we mean that their wavelength ranges are substantially the same and preferably also their power output as a function of wavelength over the wavelength range are substantially the same. Since the respective output beams from each SLED-SOA pair are linearly polarized, if the beams are combined with their polarization axes orthogonal to each other by a suitable beam combiner, then the resultant combined beam will be substantially unpolarized. Alternatively, the beams could be combined with their polarization axes aligned with each other so the resultant combined beam is also linearly polarized.

Figure 17:
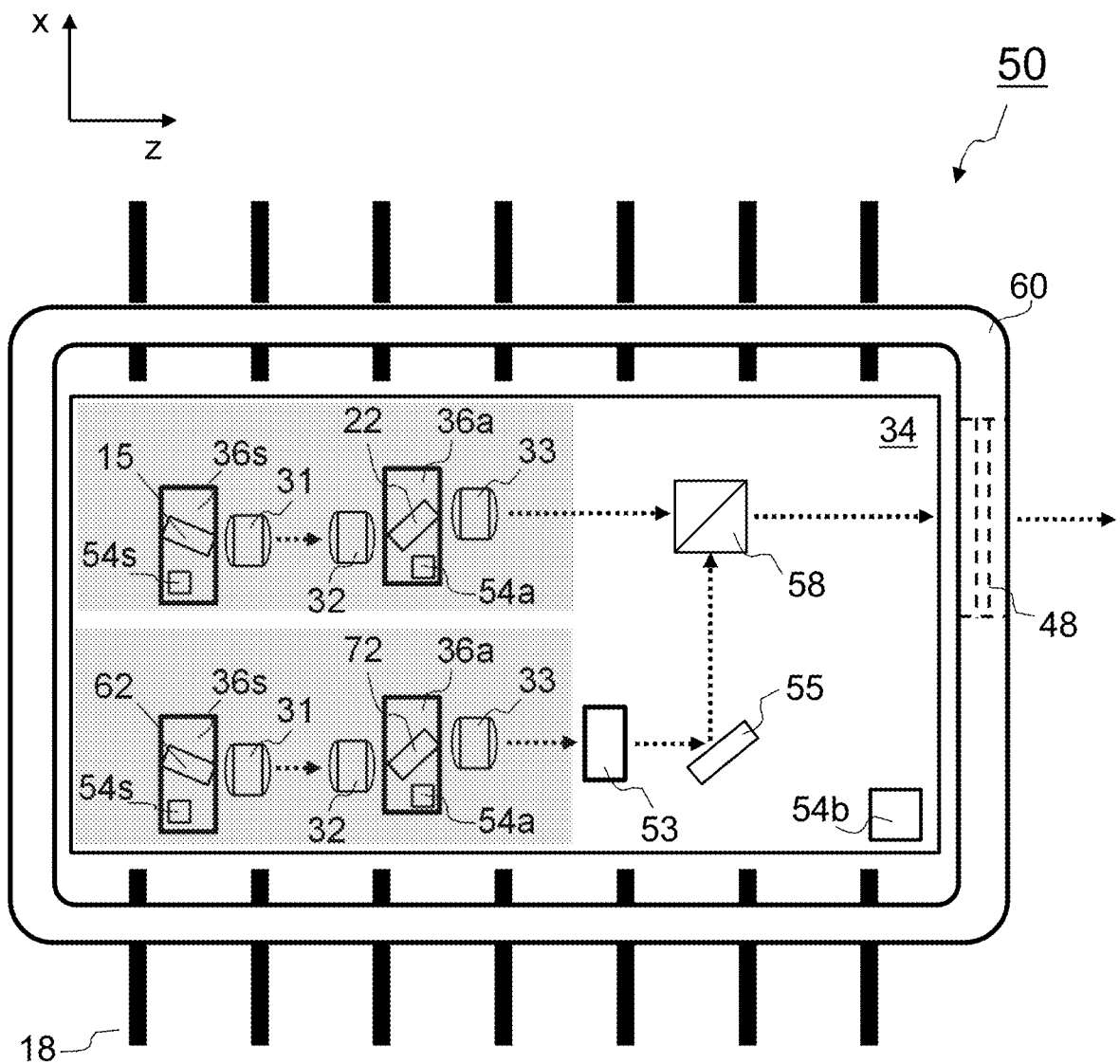
FIG. 17 is a schematic plan view of an ASE source module according to a fifth embodiment.

FIG. 17 is a schematic plan view of a source module according to a fifth embodiment. The fifth embodiment incorporates two ASE sources whose respective output beams are combined into a combined output beam. The first pair of SLED and SOA 15, 22 and their associated components (illustrated by the upper shaded box) correspond to the components of the second embodiment (FIG. 14). The second pair of SLED and SOA 62, 72 and their associated correspondence (illustrated by the lower shaded box) also correspond to the components of the second embodiment (FIG. 14). The output beam from each ASE source is linearly polarized, i.e. horizontal TE polarization aligned in the x-direction. A polarization rotating component 53, such as a half-wave plate, is arranged in the output beam path of the second pair to rotate the linearly polarized output through 90° so that its polarization axis is aligned with the y-direction. The polarization rotated beam output from the second source pair is then combined with the output beam from the first source pair by a plane mirror 55, which deflects the second source pair beam by 90° into the x-direction (with its polarization axis remaining in the y-direction), and a polarization beam splitter (PBS) 58. The combined beam thus is pseudo-unpolarized, being the combination of two linearly polarized beams of orthogonal polarization. The combined beam is then emitted from PBS 58 travelling in the z-direction and out of the module by passing through the window 48. For example, it could be that each SLED-SOA device delivers 150 mW of broadband light output and the combined output after the PBS has a power of say 250-280 mW taking account of some losses in the PBS and other optical elements in the beam path. We also note that, to avoid having to provide a polarization rotator 53, one of the SLED-SOA pairs could be mounted on its mounts 36s, 36a (or a common larger mount that could be represented in the figure by one of the shaded rectangles) such that the SLED and SOA are physically rotated by 90 degrees.

Another type of module where the light output of two, three or more SLED-SOA device pairs can be combined with one or more suitable beam combiners is with wavelength-division multiplexing (WDM). In other words, the respective wavelength ranges of each SLED-SOA pair are different. Each SLED-SOA device pair thus delivers broadband light with a different center wavelength. The wavelength ranges may be chosen to overlap at their ends so that the multiple device pairs produce a combined output beam spanning a wider wavelength range with power across the whole wider wavelength range. Alternatively, there may be gaps between each wavelength range.

Figure 18:
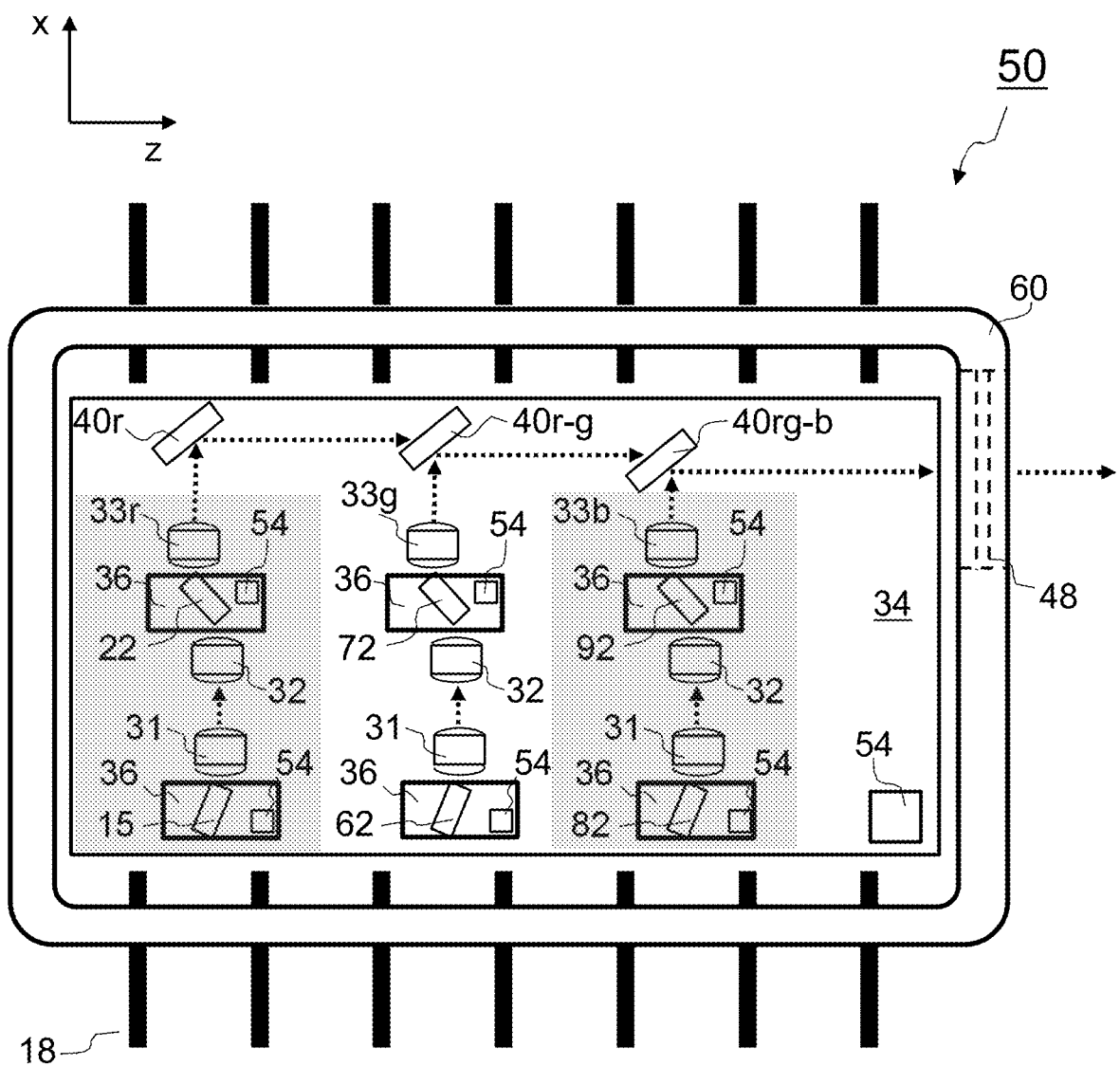
FIG. 18 is a schematic plan view of an ASE source module according to a sixth embodiment.

FIG. 18 is a schematic plan view of a source module according to a sixth embodiment. The sixth embodiment incorporates three ASE sources whose respective output beams are combined into a common output beam. The first pair of SLED and SOA 15, 22 and their associated components (illustrated by the left-hand shaded box) correspond to the components of the second embodiment. The second pair of SLED and SOA 62, 72 and their associated correspondence (illustrated by the unshaded region between the left-hand and right-hand shaded boxes) also correspond to the components of the second embodiment. The third pair of SLED and SOA 82, 92 and their associated components (illustrated by the right-hand shaded box) also correspond to the components of the second embodiment. By way of example and also for ease of description, we assume that the first source pair emits a red beam, the second source pair a green beam and the third source pair a blue beam. The red SLED beam after collimation by lens 33r is deflected through 90 degrees from the negative-x direction into the z-direction by a mirror 40r arranged at 45 degrees to x and z. The z-travelling red beam is incident on the back face of a beam combiner 40r-g which has the function of combining the red beam with the green beam. The beam combiner 40r-g is a planar optical element which is made of a suitable glass or crystal material. The beam combiner 40r-g has a front side and a back side. The red beam is incident on the back side of the beam combiner 40r-g at an angle of incidence which causes the beam to refract into the beam combiner 40r-g. The back side is preferably coated with an antireflection coating that is effective for the wavelength range, angle of incidence and polarization state of the red beam. The red beam is then routed through the glass or crystal to the front side and is once more refracted as it outputs from the front side. The front side of the beam combiner 40r-g is arranged to receive the green beam propagating in the positive-x direction from the collimating lens 33g at a position on the front surface that is the same as where the red beam passes through the front surface. Moreover, the beam combiner 40r-g is configured and arranged so that the green beam reflected from its front surface propagates in the same direction as the red beam output from the front surface, preferably the z-direction as schematically illustrated. The red and green beams thus emerge from the beam combiner 40r-g as a combined beam propagating in free space within the enclosure in direction z. The beam combiner 40r-g will usually be planar, but if desired it could be slightly curved, but still substantially planar, to provide some focusing or defocusing of one or more of the red and green beams.

The combined red and green beam is then combined with the blue beam in a similar way using a further beam combiner labelled 40rg-b. Namely, the blue beam output from the blue ASE source 82, 92 travelling in the positive x-direction is collimated by collimating lens 33b and is incident on the front surface of the beam combiner 40rg-b, and the back surface of the beam combiner 40rg-b receives the combined red-green beam. The red, blue and green beams thus emerge from the beam combiner 40rg-b as a combined beam, propagating in free space within the enclosure along an optical path in direction z. The combined beam is then output from the module by passing through the window 48. As an aside, it is noted that a variant with fibre output as described for some of the other embodiments is also possible.

The three ASE sources may be in the red, green and blue wavelength ranges respectively. However, other wavelength ranges and combinations thereof are possible, limited only by what can be fabricated with available semiconductor crystal materials. While red, green and blue colors are technically significant for display and projection applications, it will be understood that they may be generalized to mean first, second and third different emission wavelength bands from first, second and third ASE sources. Moreover, one or more of these bands need not be in the visible region, since for example one or more of the bands may be in the near infrared, or near ultraviolet.

Example (RGB): A first SLED-SOA device with a FWHM bandwidth of 5 nm at a center wavelength of 450 nm (blue) and with 150 mW output power, a second SLED-SOA device with a FWHM bandwidth of 5 nm at a center wavelength of 515 nm (green) and with 200 mW output power, and a third SLED-SOA device with a FWHM bandwidth of 5 nm at a center wavelength of 635 nm (red) and with 200 mW output power. The WDM-combined output of all three SLED-SOA devices spans a represent a SLED-based RGB light source with high output power that could be used in projection systems, for example.

Example (NIR): A first SLED-SOA device with a FWHM bandwidth of 30 nm at a center wavelength of 820 nm and with 150 mW output power, a second SLED-SOA device with a FWHM bandwidth of 30 nm at a center wavelength of 840 nm and with 150 mW output power, and a third SLED-SOA device with a FWHM bandwidth of 30 nm at a center wavelength of 860 nm and with 150 mW output power. The WDM-combined output of all three SLED-SOA devices spans a FWHM spectral bandwidth ranging from 805 nm to 875 nm (i.e. 70 nm FWHM) with a combined output power of 350-450 mW, considering some losses in the WDM combiner or other optical elements.

The beam combiners could have any of the following features. The beam combiners could have polarizing beam splitter properties in that they behave in a way that depends on the polarization state of the incident light to reflect one polarization (e.g. TE/horizontal) and transmit another (e.g. TM/vertical) or vice versa. The beam combiners may reflect or transmit depending on whether the incident light is above or below a threshold wavelength, such as reflecting shorter wavelengths and transmitting longer wavelengths or vice versa in the manner of a combiner used for wavelength division multiplexing applications. The beam combiners may also be provided with different splitting ratios as desired, e.g. for power balancing and to tap off a portion of the power for power monitoring. It will be understood that the ASE module with three-ASE source devices described above can be modified to remove one of the ASE source devices to provide corresponding two ASE device module.

The beam combiners which receive a light beam on their back faces preferably have antireflection coatings on their back faces. Each AR coating will typically be optimized for the incident wavelength range, the incident angle and the incident polarization state of the incident beam. The beam combiners may additionally or instead have integrally formed on their back faces, and/or their front faces, coatings for other purposes such as wavelength-dependent filtering, e.g. an edge filter, and polarization, e.g. linear polarizer.

While the illustrated embodiment has three ASE sources, further embodiments may be implemented with four, five, six or more ASE sources. The ASE sources are preferably arranged on a common substrate 34. The SLEDs and SOAs are integrated in a common package as described in the above embodiments for three ASE sources. With higher numbers of ASE sources, larger packages may be needed, e.g. butterfly packages with more than 14 pins that have more internal volume. Four or more ASE source devices may be beneficial for achieving a desired specification, for example to span a wider spectrum than would be possible with three ASE sources, or to combine visible (e.g., RGB) ASE emitters with NIR ASE emitters or LDs to support multiple modes of use (modalities) in a single module. One concrete example, would be to have an optical module accommodating one group of, e.g. 2 or 3, ASE sources for RGB output (e.g., for color fundus imaging) and another group of, e.g. 3, ASE sources for high-resolution (HR) OCT. Another concrete example would be a module with a combined ASE source (e.g. with 3 ASE source devices) for HR-OCT in the wavelength range 780-930 nm and a further single ASE source device with a center wavelength of around 750 nm for scanning laser ophthalmoscopy (SLO) and/or eye tracking.

A further variation would be that the SOA may not be needed for all SLEDs, so one or more of the ASE sources may be replaced with a SLED without subsequent SOA.

It will be understood that references to a combined beam could be taken to imply that the different ASE sources, i.e. SLED-SOA pairs, are driven to simultaneously emit. However, this is not necessarily the case. For a display or projection application, red, green and blue beams may emit simultaneously or may be emitted in a sequential scheme in which each color is emitted in a short time slot with a duration of a few nanoseconds, microseconds or milliseconds, and a certain sequence of color-specific time slots is repeated periodically. However, for other applications, the different ASE sources may be driven selectively and not all be active at the same time. For example, if the module is intended for a multi-modality system requiring say one group of one or more ASE sources to emit in the NIR for OCT and another group of one or more ASE sources to emit in the visible for fundus imaging, then these two groups would not generally be operated simultaneously, but these two groups are nevertheless arranged in the module to have a combined beam path, i.e. so that their beams are (or would be) combined when (or if) they are simultaneously emitted.

In the above module embodiments, attachment of the components to the main board 34, the submounts 36 and the housing 60 may be by adhesive bonding, e.g. with a UV-curable epoxy resin. (Alternatively a thermally activated epoxy resin may be used for some or all of the components. Moreover, another option is for a solder process to be used for some or all the components.) The attachment is done with high-accuracy placement. Active alignment, i.e. with the SLED and ASE sources switched on during alignment, may be used during the component attachment to ensure that the different optical components are correctly located for guiding and combining the different beams as desired. Active alignment may also help ensure efficient coupling into an output fibre or that a free-space beam has the desired output direction, position and focal properties (e.g. is precisely collimated or with a focus at a specified distance from the module). After UV-curing of the epoxy resin, the main board 34 with its attached components may be baked in an oven. It will be appreciated the components may not be single components as illustrated, but may each consist of two or more components, such as isolators (electrical, thermal and/or vibration), and submounts. Moreover, physically separate filters, polarizers, apertures or other optical components (not illustrated) may also be included that are attached to the mounting board 34.

Figure 19:
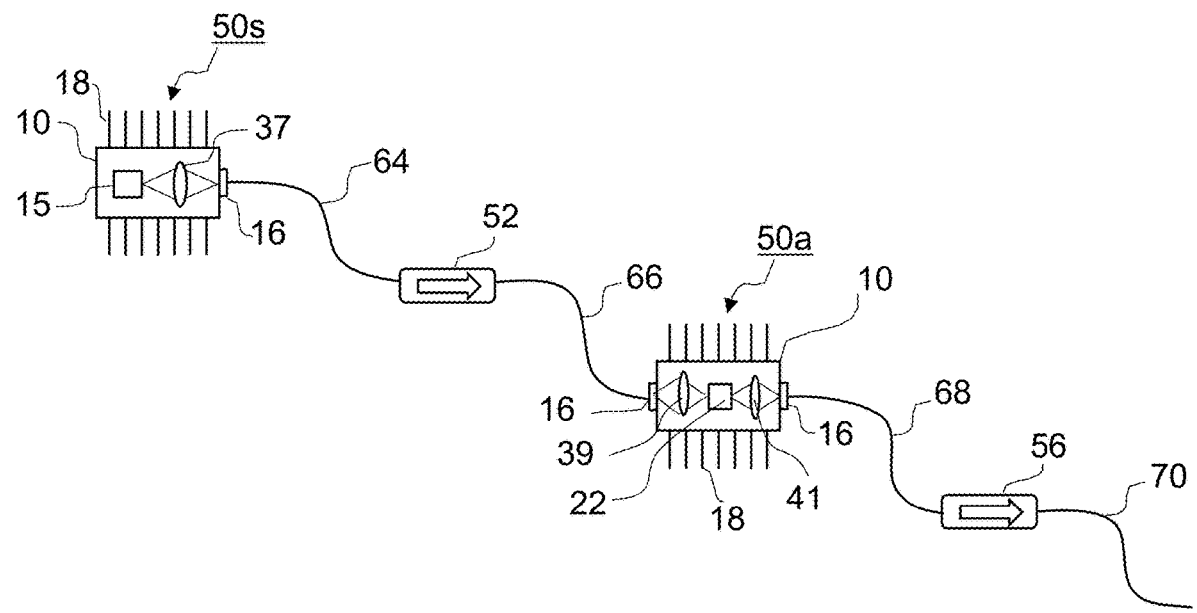
FIG. 19 is a schematic plan view of an ASE source according to a seventh embodiment.

FIG. 19 is an embodiment with an alternative construction. A single ASE source 15, 22 is provided, but in this embodiment the SLED 15 and SOA 22 are accommodated in different butterfly packages 50s and 50a. The two butterfly packages 50s, 50a are interconnected optically by optical fibre. The optical fibre connection is illustrated as being effected in first and second fibre sections 64, 66 with an optical isolator (or attenuator or polarization manipulator) 52 arranged in series between the sections. In the first butterfly package 50*s*, a lens 37 is arranged to focus the SLED's output beam onto the end of fibre section 64 held in ferrule 16. In the second butterfly package 50*a*, a lens 39 focuses the light received from the SLED 15 as output from the end of fibre section 66, which is held in a ferrule 16, onto one end of the SOA 22. A further lens 41 is arranged to focus the output from the SOA 22 onto the end of a fibre section 68 held in a ferrule 16. The output beam travelling through the fibre section 68 is supplied to an isolator (or attenuator) 56, the output of which is connected to a further fibre section 70 via which the light is finally output for downstream use. Functionally, in terms of its active components, this embodiment is thus analagous to the third embodiment (FIG. 15). Moreover, similar variations as between, and discussed for, the above module embodiments are possible.

Referring generally to the various module designs discussed above, the paired SLED and SOA could be realized by two separate chips that can be mounted on separate submounts or on the same submount. In certain embodiments, one or more of the chips may be part of a photonics integrated circuit (PIC), for example the PIC may incorporate mounting pads for the SLED, SOA or combined SLED/SOA chips. This would represent a so-called "hybrid" integration of active semiconductor devices like the SLED and SOA with passive semiconductor PIC devices, optionally also with micro-optical components such as lenses, mirrors, filters, polarizers, beam combiners and other optics.

Figure 20:
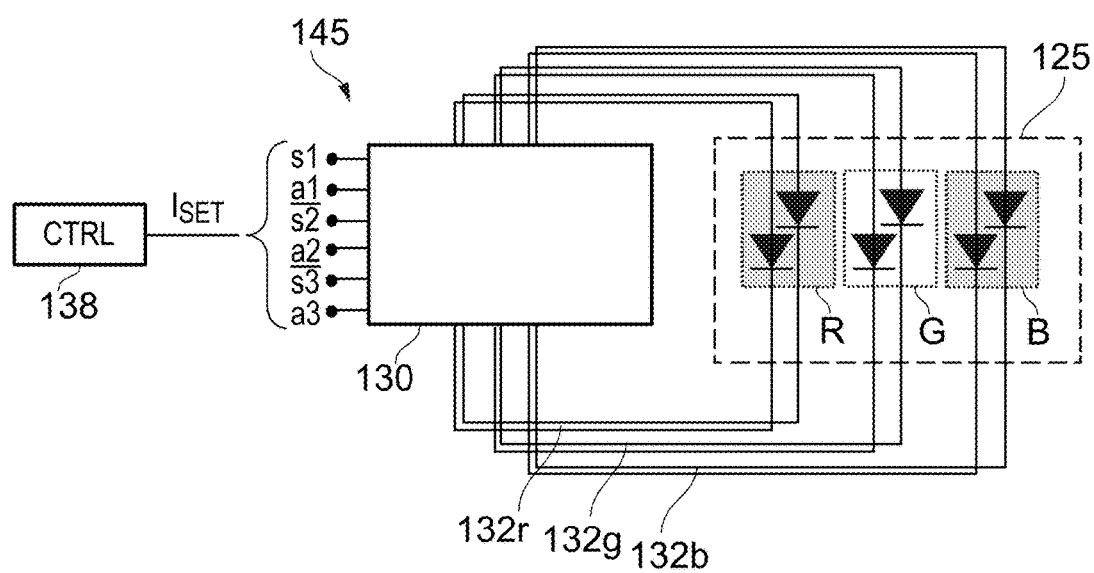
FIG. 20 is a schematic drawing of a drive circuit and other components suitable for integration of an ASE source device or module embodying the invention.

FIG. 20 is a schematic drawing of a light source unit 145 including a drive circuit and other components suitable for integration of a three-emitter SLED/SOA device or module 125 embodying the invention, the three emitters, each with one SLED and one SOA, being labelled R, G and B for red, green and blue. The three SLED/SOA emitters are driven by respective dual current supply lines 132*r*, 132*g* and 132*b* from a driver unit 130 which receives respective drive currents ISET from a controller 138 for each of the six components, i.e. R, G and B SLEDs and R, G and B SOAs, these currents being labelled s1, a1; s2, a2; and s3, a3 for the SLEDs and SOAs respectively.

Some system applications employing modules as described above are now discussed.

Figure 21:
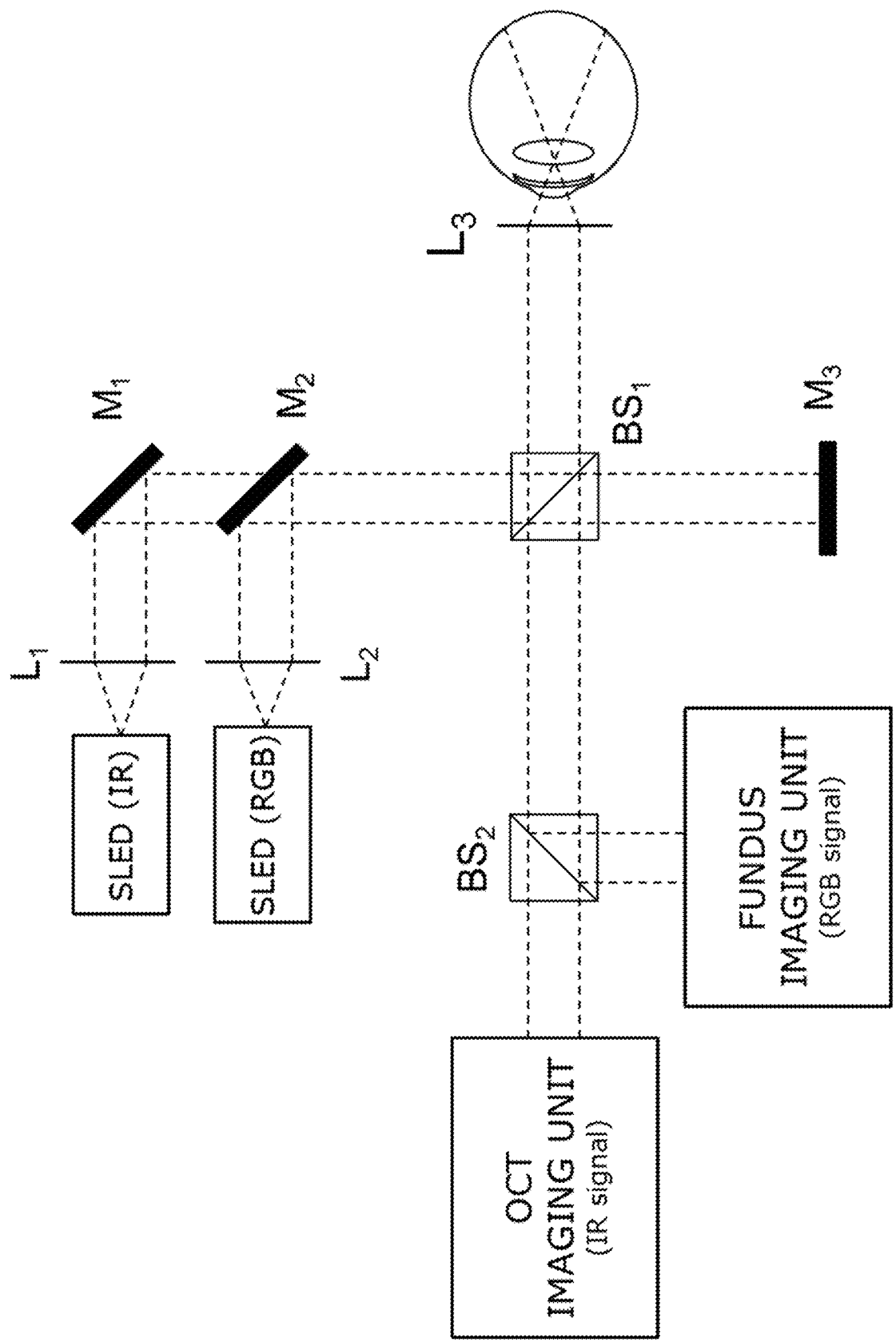
FIG. 21 is a schematic diagram of an example combined OCT and fundus imaging system which comprises two ASE source modules embodying the invention.

FIG. 21 is a schematic drawing of a combined OCT and fundus imaging system for obtaining images of a human or mammalian eye employing two ASE source modules as described above, one with IR output band for OCT imaging and another with a visible (RGB) output band for fundus imaging. The specification of the RGB ASE source module is, for example: a blue ASE source with a center wavelength of 455 nm and a 3-dB bandwidth of 10 nm, a green ASE source with a center wavelength of 510 nm and a 3-dB bandwidth of 10 nm, and a red ASE source with a center wavelength of 650 nm and a 3-dB bandwidth of 10 nm. The specification of the IR output may be met by a single IR ASE source, for example an ASE source with a center wavelength of 845 nm, 3 dB bandwidth of 145 nm, 10 dB bandwidth of 165 nm, 10 dB wavelength range of 765-930 nm, 10 mW output power and a coherence length of 2.9 micrometers. It will be appreciated this output is from the red end of the visible to near-infrared, which is suitable for OCT systems. The parts shown are as follows:

| | |
|---|---|
| SLED (IR) | IR source module |
| SLED (RGB) | RGB/white-light source module |
| BS1, BS2 | beam splitters |
| L1 | lens |
| M1, M2, M3 | mirrors |

Each ASE module outputs a collimated, circular or elliptical section beam. The collimated beams are reflected 90 degrees by plane mirrors M1 and M2 into a common path, wherein mirror M2 allows the IR ASE beam to pass through it and combine with the RGB ASE beam at the front face of mirror M2. A beam splitter BS1 is arranged to reflect the IR and ASE beam into a path, called the sample arm, that features a focusing lens L1, which focuses the ASE beams onto a desired focal plane on the eye, e.g. cornea, lens, pupil or retina. A certain portion of the IR/RGB light is transmitted at beam splitter BS1 into a separated path, called the reference arm, which incorporates another mirror M3 that reflects the IR/RGB light and that has a path length that is matched to the path length of the sample arm. The light which is backscattered from the eye is directed back through the same path until beam splitter BS1, where the IR light of both sample and reference arm interfere. At the beam splitter BS1 the backscattered component passes through without reflection to a second beam splitter BS2 which allows the IR component of the light to pass through it and be received by an OCT imaging unit and which reflects the RGB component of the light by 90 degrees into a fundus imaging unit. We have illustrated a specific static-field OCT/fundus imaging configuration, by way of example only, but the ASE source module is also suitable for use in a scanning field OCT/fundus system. Example applications of the IR ASE source module include: spectral-domain or Fourier-domain OCT where the beam is focused to a small point of high lateral resolution and scanned in two dimensions across an object; spectral-domain or Fourier-domain line-field OCT imaging where the beam is focused to a narrow line and scanned in one dimension across an object; spectral-domain or Fourier-domain full-field OCT imaging where the beam is kept static and not scanned across an object; spectral-domain or Fourier-domain optical coherence microscopy (OCM) where the beam is focused to a small point or narrow line and scanned across an object. The beam might also be spatially modulated, e.g., by using digital mirror devices, spatial light modulators or similar. It will be understood that either the OCT-specific or the fundus-specific components could be removed from the illustrated system to make a fundus system or an OCT system respectively.

Figure 22:
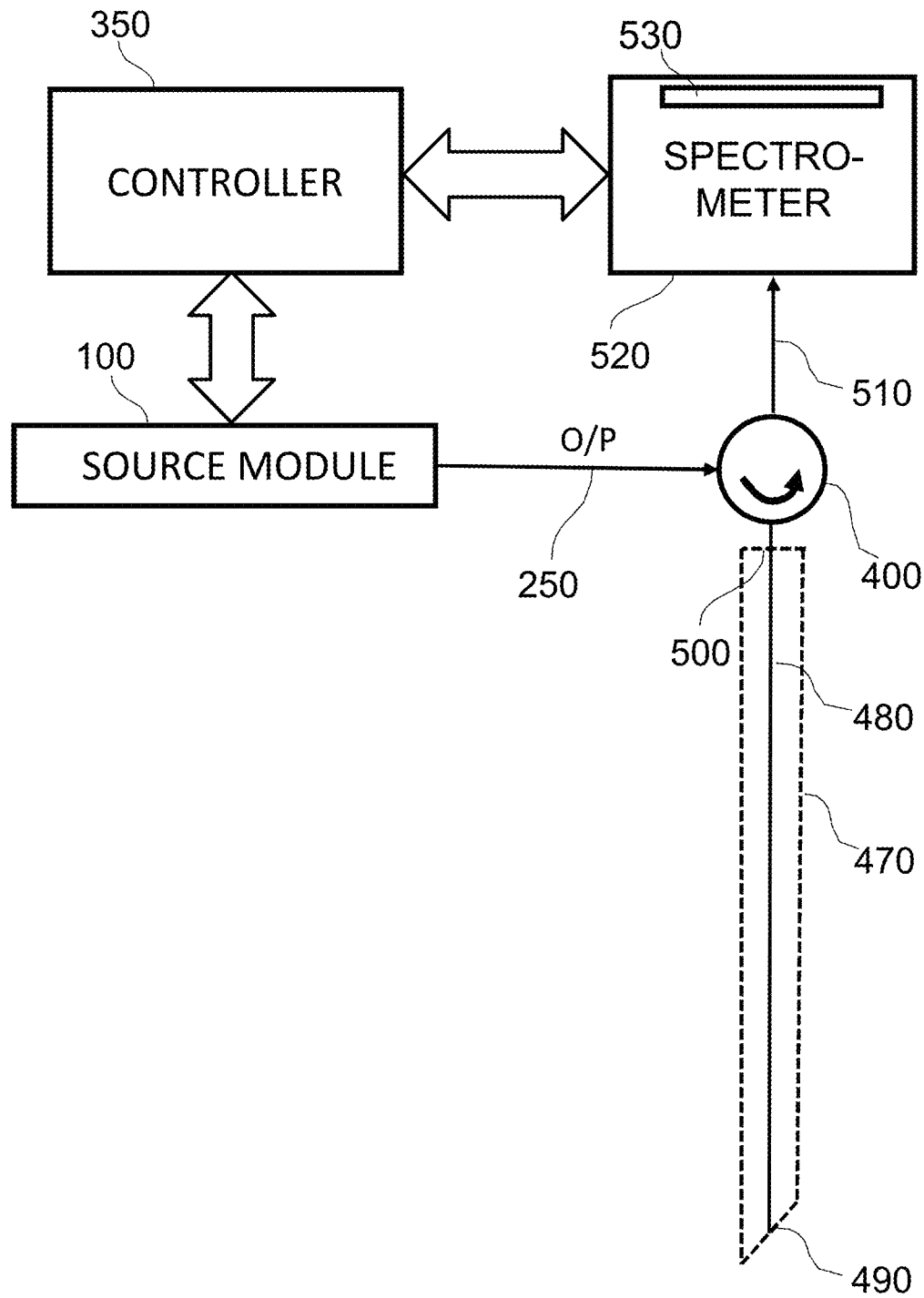
FIG. 22 is a schematic drawing of a medical device system comprising an ASE source device or module embodying the invention, and downstream optical components, wherein the downstream optical components form an endoscopic, laparoscopic, bronchoscopic or catheter-like medical device.

FIG. 22 is a schematic drawing of a medical device system comprising an ASE module 100 as described above and downstream optical components that form an endoscopic, laparoscopic, bronchoscopic or catheter-like medical device. An optical path 250 connects the source module 100 and an optical circulator 400. The system further comprises an insertion tube 470, which may be rigid or flexible, suitable for insertion into a patient, for example into a bodily orifice, such as a blood vessel, digestive tract, lung, colon, esophagus etc. The insertion tube 470 includes a light guide 480 which may be formed entirely or in part from an optical fiber or optical fiber bundle, or may be a hollow light guiding tube or some other light guide, and may include free-space optical elements such as lenses, e.g. for collimating, coupling in, coupling out and focusing. The light guide terminates at or near a distal tip 490 of the insertion tube. Light from the source module 100 is supplied to the distal tip 490 via the circulator 400 and any necessary coupling optics (not shown) between the circulator 400 and proximal end 500 of the insertion tube. Light collected from the sample area adjacent the distal tip 490 of the insertion tube 470, e.g. by scattering or fluorescence, may be guided back to the detection optics also by the same light guide 480 that conveyed the excitation light, or via a different light guide (not shown) arranged in the insertion tube 470. The collected light passes through the circulator 400 via a light path 510 to a spectrometer 520 and light detector 530. If no spectral filtering of the collected light signal is needed, then a spectrometer will of course not be present prior to the light detector. The light detector 530 may be an array detector such as a charged coupled device (CCD) or photodiode array, or a light detector without spatial resolution, e.g. a single photodiode. The system is under the control of a controller 350 via control lines schematically illustrated with double-headed arrows which may additionally have data processing functionality, e.g. for image processing or other data analysis of signals received at the detector 530. Alternatively, measurement data may be passed, e.g. by the controller, to a separate computing apparatus for image processing and/or data analysis. Another variation would be to replace the circulator with a fused fiber coupler or free-space coupler. As well as one or more ASE sources, the source module 100 may also include a LD which can be used for surgical purposes, such as polyp removal.

Figure 23:
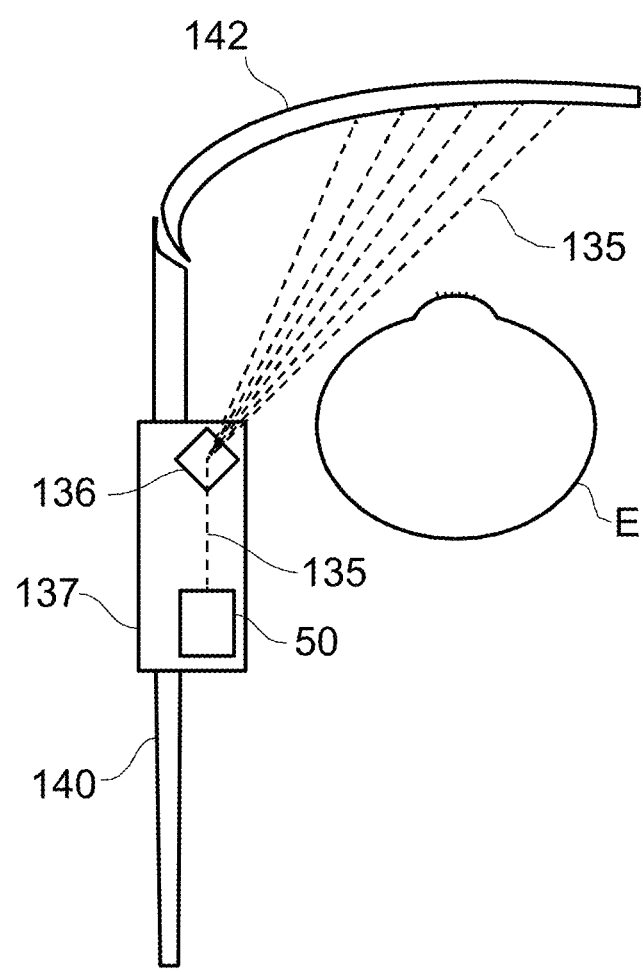
FIG. 23 shows an example projection system comprising an ASE source module embodying the invention.

FIG. 23 shows an example projection system in a monocle format, i.e. glasses or spectacles for a single eye. A housing 137 is integrated midway along a temple 140 and houses an RGB source module 50 according to FIG. 18 as well as a drive circuit according to FIG. 20 (not shown). The combined RGB light beam 135 output by the RGB source module 50 is directed to a scanning element 136 which projects an image on the inside surface of a lens 142 which can be viewed by the wearer's eye E. An image is thus formed on the inside surface of the lens for the wearer to view conventionally. (Alternatively, lens 142 could form a reflection surface for direct retinal projection onto the retina of the wearer's eye E. It will be understood that the reference to the lens 142 does not imply that the lens 142 has any lensing function insofar as the projection system is concerned, rather it merely serves to provide a projection surface for conventional projection (or a reflection surface for direct projection). It will be understood that the monocle format could be doubled up to provide glasses in a spectacles format, wherein a spectacles format allows for additional possibilities, such as stereoscopic imaging for 3D.

It will be clear to one skilled in the art that many improvements and modifications can be made to the foregoing exemplary embodiments without departing from the scope of the present disclosure.

The invention claimed is:

1. An amplified spontaneous emission, ASE, source device comprising:
a superluminescent light emitting diode, SLED, and a semiconductor optical amplifier, SOA, arranged in series, each having a structure made up of a succession of epitaxial semiconductor layers which form an optical mode confining waveguide comprising a core of a higher refractive index active region layer, and a cladding of lower refractive index cladding layers,
wherein the SLED and the SOA each have a confinement factor defined as the percentage of the power of the optical mode that lies within the active region layer, wherein the confinement factor of the SLED is greater than that of the SOA by a factor of at least 1.2,
wherein the SLED and the SOA each have a spectral bandwidth defined by their respective 10 dB power values, the spectral bandwidth of the SLED being greater than that of the SOA by at least 20% in wavelength terms.

2. The ASE source device of claim 1, wherein the SLED and the SOA each have a confinement factor defined as the percentage of the power of the optical mode that lies within the active region layer, wherein the confinement factor of the SLED is greater than that of the SOA by a factor of at least 1.3.

3. The ASE source device of claim 1, wherein the SLED and the SOA each have a vertical confinement factor component, defined as the percentage of the power of the optical mode in the vertical direction that lies within the active region layer, and wherein the vertical confinement factor component of the SLED is greater than that of the SOA by a factor of at least 1.2.

4. The ASE source device of claim 1, wherein the SLED and the SOA each have a lateral confinement factor component, defined as the percentage of the power of the optical mode in the horizontal direction that lies within the active region layer, and wherein the lateral confinement factor component of the SLED is greater than that of the SOA by a factor of at least 1.2.

5. The ASE source device of claim 1, wherein the thickness of the active region layer of the SLED is greater than that of the SOA by a factor of at least 1.2.

6. The ASE source device of claim 1, wherein the SLED and the SOA each comprise a ridge to define the lateral extent of their respective optical modes, wherein the ridge of the SOA has an average width greater than that of the SLED by a factor of at least 1.2.

7. The ASE source device of claim 1, wherein the SLED and the SOA each comprise an injection electrode operable to inject carriers into the active region layer, and wherein the injection electrode of the SOA has an average width greater than that of the SLED by a factor of at least 1.2.

8. The ASE source device of claim 1, wherein the epitaxial semiconductor layers of the SLED and SOA are arranged on a common semiconductor substrate.

9. The ASE source device of claim 1, wherein the SLED and SOA are arranged on separate semiconductor substrates, which are attached to a common submount.

10. An amplified spontaneous emission, ASE, source module comprising:
a first ASE source device operable to emit a first beam having a first wavelength range, the first ASE source device comprising a first superluminescent light emitting diode, SLED, and a first semiconductor optical amplifier, SOA, arranged in series to form a first SLED-SOA pair, each having a structure made up of a succession of epitaxial semiconductor layers which form an optical mode confining waveguide comprising a core of a higher refractive index active region layer, and a cladding of lower refractive index cladding layers, wherein the first SLED and the first SOA each have a confinement factor defined as the percentage of the power of the optical mode that lies within the active region layer, wherein the confinement factor of the first SLED is greater than that of the first SOA by a factor of at least 1.2;
a second ASE source device operable to emit a second beam having a second wavelength range, the second ASE source device comprising a second superluminescent light emitting diode, SLED, and a second semiconductor optical amplifier, SOA, arranged in series to form a second SLED-SPA pair, each having a structure made up of a succession of epitaxial semiconductor layers which form an optical mode confining waveguide comprising a core of a higher refractive index active region layer, and a cladding of lower refractive index cladding layers, wherein the second SLED and the second SOA each have a confinement factor defined as the percentage of the power of the optical mode that lies within the active region layer, wherein the confinement factor of the second SLED is greater than that of the second SOA by a factor of at least 1.2; and a beam combiner arranged to receive the first and second beams and to combine them into an output beam, wherein for each of the first and second SLED-SOA pairs, the SLED and the SOA have respective spectral bandwidths defined by their respective 10 dB power values, the spectral bandwidth of the SLED being greater than that of the SOA by at least 20% in wavelength terms.

11. The ASE source module of claim 10, wherein the first and second wavelength ranges are substantially the same.

12. The ASE source module of claim 10, wherein the first and second beams are linearly polarized along respective polarization axes, and the beam combiner is arranged to receive the first and second beams with their polarization axes orthogonal to each other and to combine them into a substantially unpolarized output beam.

13. The ASE source module of claim 10, wherein the first and second wavelength ranges are different, and overlap at their ends to produce an output beam having power across a continuous range of wavelengths made up of the combined first and second wavelength ranges.

14. The ASE source module of claim 10, further comprising:

a third ASE source device operable to emit a third beam having a third wavelength range, the third ASE source device comprising a third superluminescent light emitting diode, SLED, and a third semiconductor optical amplifier, SOA, arranged in series, each having a structure made up of a succession of epitaxial semiconductor layers which form an optical mode confining waveguide comprising a core of a higher refractive index active region layer, and a cladding of lower refractive index cladding layers, wherein the third SLED and the third SOA each have a confinement factor defined as the percentage of the power of the optical mode that lies within the active region layer, wherein the confinement factor of the third SLED is greater than that of the third SOA by a factor of at least 1.2; and a further beam combiner arranged to receive the already combined first and second beams and the third beam and to combine them into an output beam.

15. The ASE source module of claim 14, wherein the first, second and third wavelength ranges are different, and overlap at their ends to produce an output beam having power across a continuous range of wavelengths made up of the combined first, second and third wavelength ranges.

16. An optical coherence tomography system comprising:

an ASE source device arranged to direct its output into a light guide, the ASE source device comprising a superluminescent light emitting diode, SLED, and a semiconductor optical amplifier, SOA, arranged in series, each having a structure made up of a succession of epitaxial semiconductor layers which form an optical mode confining waveguide comprising a core of a higher refractive index active region layer, and a cladding of lower refractive index cladding layers, wherein the SLED and the SOA each have a confinement factor defined as the percentage of the power of the optical mode that lies within the active region layer, wherein the confinement factor of the SLED is greater than that of the SOA by a factor of at least 1.2, wherein the SLED and the SOA each have a spectral bandwidth defined by their respective 10 dB power values, the spectral bandwidth of the SLED being greater than that of the SOA by at least 20% in wavelength terms; and a beam splitter arranged to receive light output from the ASE source device and to direct one component into a first, sample arm to a sample position and another component to a second, reference arm, and to recombine light received back from the first and second arms and direct the recombined light to a detector.

17. A fundus imaging system comprising:

an ASE source device arranged to direct its output into a light guide, the ASE source device comprising a superluminescent light emitting diode, SLED, and a semiconductor optical amplifier, SOA, arranged in series, each having a structure made up of a succession of epitaxial semiconductor layers which form an optical mode confining waveguide comprising a core of a higher refractive index active region layer, and a cladding of lower refractive index cladding layers, wherein the SLED and the SOA each have a confinement factor defined as the percentage of the power of the optical mode that lies within the active region layer, wherein the confinement factor of the SLED is greater than that of the SOA by a factor of at least 1.2, wherein the SLED and the SOA each have a spectral bandwidth defined by their respective 10 dB power values, the spectral bandwidth of the SLED being greater than that of the SOA by at least 20% in wavelength terms; and an optical arrangement configured to direct light output from the ASE source device to a sample position and collect light received back from the sample position into a fundus imaging unit.

18. An endoscopic imaging system comprising:

an ASE source device arranged to direct its output into a light guide, the ASE source device comprising a superluminescent light emitting diode, SLED, and a semiconductor optical amplifier, SOA, arranged in series, each having a structure made up of a succession of epitaxial semiconductor layers which form an optical mode confining waveguide comprising a core of a higher refractive index active region layer, and a cladding of lower refractive index cladding layers, wherein the SLED and the SOA each have a confinement factor defined as the percentage of the power of the optical mode that lies within the active region layer, wherein the confinement factor of the SLED is greater than that of the SOA by a factor of at least 1.2, wherein the SLED and the SOA each have a spectral bandwidth defined by their respective 10 dB power values, the spectral bandwidth of the SLED being greater than that of the SOA by at least 20% in wavelength terms; and an insertion tube adapted for insertion into a bodily orifice in which is arranged at least a part of the light guide, wherein the light guide terminates proximal a distal end of the insertion tube.

19. A projection system comprising an amplified spontaneous emission, ASE, source module comprising:

a first ASE source device operable to emit a first beam having a first wavelength range, the first ASE source device comprising a first superluminescent light emitting diode, SLED, and a first semiconductor optical amplifier, SOA, arranged in series to form a first SLED-SOA pair, each having a structure made up of a succession of epitaxial semiconductor layers which form an optical mode confining waveguide comprising a core of a higher refractive index active region layer, and a cladding of lower refractive index cladding layers, wherein the first SLED and the first SOA each have a confinement factor defined as the percentage of the power of the optical mode that lies within the active region layer, wherein the confinement factor of the first SLED is greater than that of the first SOA by a factor of at least 1.2;

a second ASE source device operable to emit a second beam having a second wavelength range, the second ASE source device comprising a second superluminescent light emitting diode, SLED, and a second semiconductor optical amplifier, SOA, arranged in series to form a second SLED-SOA pair, each having a structure made up of a succession of epitaxial semiconductor layers which form an optical mode confining waveguide comprising a core of a higher refractive index active region layer, and a cladding of lower refractive index cladding layers, wherein the second SLED and the second SOA each have a confinement factor defined as the percentage of the power of the optical mode that lies within the active region layer, wherein the confinement factor of the second SLED is greater than that of the second SOA by a factor of at least 1.2;

a beam combiner arranged to receive the first and second beams and to combine them into an output beam;

a third ASE source device operable to emit a third beam having a third wavelength range, the third ASE source device comprising a third superluminescent light emitting diode, SLED, and a third semiconductor optical amplifier, SOA, arranged in series to form a third SLED-SOA pair, each having a structure made up of a succession of epitaxial semiconductor layers which form an optical mode confining waveguide comprising a core of a higher refractive index active region layer, and a cladding of lower refractive index cladding layers, wherein the third SLED and the third SOA each have a confinement factor defined as the percentage of the power of the optical mode that lies within the active region layer, wherein the confinement factor of the third SLED is greater than that of the third SOA by a factor of at least 1.2; and a further beam combiner arranged to receive the already combined first and second beams and the third beam and to combine them into an output beam, wherein the first, second and third wavelength ranges represent three complementary colors of a color palette for additive mixing, wherein for each of the first, second and third SLED-SOA pairs, the SLED and the SOA have respective spectral bandwidths defined by their respective 10 dB power values, the spectral bandwidth of the SLED being grater than that of the SOA by at least 20% in wavelength terms.

* * * * *